United States Patent
Tanaka et al.

(10) Patent No.: US 10,763,050 B2
(45) Date of Patent: Sep. 1, 2020

(54) PHOTOELECTRIC CONVERSION ELEMENT

(71) Applicants: Yuuji Tanaka, Shizuoka (JP); Tsuyoshi Matsuyama, Shizuoka (JP); Ryota Arai, Shizuoka (JP); Tokushige Kino, Shizuoka (JP); Shigeyo Suzuki, Shizuoka (JP); Naomichi Kanei, Shizuoka (JP)

(72) Inventors: Yuuji Tanaka, Shizuoka (JP); Tsuyoshi Matsuyama, Shizuoka (JP); Ryota Arai, Shizuoka (JP); Tokushige Kino, Shizuoka (JP); Shigeyo Suzuki, Shizuoka (JP); Naomichi Kanei, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 136 days.

(21) Appl. No.: 16/043,876

(22) Filed: Jul. 24, 2018

(65) Prior Publication Data
US 2018/0330890 A1 Nov. 15, 2018

Related U.S. Application Data

(63) Continuation of application No. PCT/JP2017/001592, filed on Jan. 18, 2017.

(30) Foreign Application Priority Data

Jan. 25, 2016 (JP) .................................. 2016-011564
Sep. 2, 2016 (JP) .................................. 2016-171886

(51) Int. Cl.
*H01G 9/20* (2006.01)
*H01L 51/42* (2006.01)
(Continued)

(52) U.S. Cl.
CPC ......... *H01G 9/2018* (2013.01); *C07C 217/92* (2013.01); *H01G 9/2013* (2013.01);
(Continued)

(58) Field of Classification Search
None
See application file for complete search history.

(56) References Cited

U.S. PATENT DOCUMENTS

| 4,927,721 A | 5/1990 | Gratzel et al. |
| 6,084,176 A | 7/2000 | Shiratsuchi et al. |
| 2017/0069431 A1 | 3/2017 | Tanaka et al. |

FOREIGN PATENT DOCUMENTS

| CN | 104844464 A | 8/2015 |
| JP | 2664194 | 6/1997 |

(Continued)

OTHER PUBLICATIONS

International Search Report dated Feb. 21, 2017 for counterpart International Patent Application No. PCT/JP2017/001592 filed Jan. 18, 2017.

(Continued)

*Primary Examiner* — Eli S Mekhlin
(74) *Attorney, Agent, or Firm* — Oblon, McClelland, Maier & Neustadt, L.L.P.

(57) ABSTRACT

Provided is a photoelectric conversion element including: a first electrode; a hole blocking layer; an electron transport layer; a hole transport layer; and a second electrode, wherein the hole transport layer contains a compound represented by general formula (1) below, (Continued)

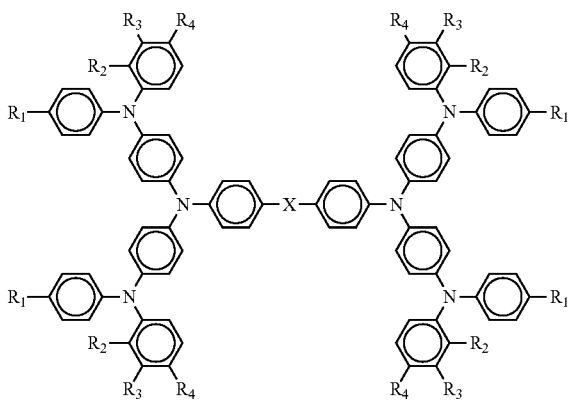

General formula (1)

where in the formula, $R_1$ represents a methoxy group or an ethoxy group, $R_2$ represents a hydrogen group or a methyl group, $R_3$ represents a hydrogen group, a methyl group, or a methoxy group, $R_4$ represents a methoxy group, and X represents —$CH_2$—, —$CH_2CH_2$—, —O—, or —C($CH_2$)$_5$—.

20 Claims, 1 Drawing Sheet

(51) Int. Cl.
*C07C 217/92* (2006.01)
*H01L 51/00* (2006.01)
*H01L 51/44* (2006.01)

(52) U.S. Cl.
CPC ....... *H01G 9/2059* (2013.01); *H01L 51/0059* (2013.01); *H01L 51/4226* (2013.01); *H01L 51/4273* (2013.01); *H01L 51/442* (2013.01); *C07C 2601/14* (2017.05); *Y02E 10/549* (2013.01)

(56) References Cited

FOREIGN PATENT DOCUMENTS

| JP | 11-144773 | 5/1999 |
|---|---|---|
| JP | 2000-106223 | 4/2000 |
| JP | 2016-178102 | 10/2016 |
| WO | WO2015/125587 A1 | 8/2015 |

OTHER PUBLICATIONS

Written Opinion dated Feb. 21, 2017 for counterpart International Patent Application No. PCT/JP2017/001592 filed Jan. 18, 2017.
Panasonic Technical Report, vol. 56, No. 4 (2008) 87 (with English Abstract).
Nature, 353 (1991) 737.
J. Am. Chem. Soc., 115 (1993) 6382.
Nature, 485 (2012) 486.
J. Am. Chem. Soc., 133 (2011) 18042.
J. Am. Chem. Soc., 135 (2013) 7378.
J. Phys. Chem. C, 116 (2012) 25721.
Fujikura Technical Report, 120 (2011) 42 (with English Abstract).
Solar Energy Materials & Solar Cells, 181 (2005) 87.
Sven Y. Brauchli et al., Factors controlling the photoresponse of copper ( I ) diamine dyes containing hole-transporting dendrons in dye-sensitized solar cells: substituent and solvent effects, RSC Advances, 2014, vol. 4, No. 66, p. 34801-34815.
Biljana Bozic-Weber et al., Hole-transport functionalized copper ( I ) dye sensitized solar cells, Physical chemistry chemical physics, 2013, p. 1-14.
J. Org. Chem., 67 (2002) 3029.

PHOTOELECTRIC CONVERSION ELEMENT

CROSS-REFERENCE TO RELATED APPLICATIONS

The present application is a continuation application of International Application No. PCT/JP2017/001592, filed Jan. 18, 2017, which claims priority to Japanese Patent Application No. 2016-011564, filed Jan. 25, 2016 and Japanese Patent Application No. 2016-171886, filed Sep. 2, 2016. The contents of these applications are incorporated herein by reference in their entirety.

BACKGROUND OF THE INVENTION

Field of the Invention

The present disclosure relates to a photoelectric conversion element.

Description of the Related Art

In recent years, driving power for electronic circuits has been significantly reduced, and it has become possible to drive various electronic parts such as sensors with a weak power. Expected uses of sensors include application to stand-alone power systems (energy harvesting elements) capable of generating and consuming power instantly. Among such energy harvesting elements, solar cells are drawing attention as elements capable of generating power at anywhere there is light. Small-sized energy harvesting elements can be disposed at various places, and when combined with secondary cells, can serve as primary cells that need no replacement. Improvement in the power generation performance will enable a greater downsizing and an increase in the number of times sensor information can be transmitted wirelessly.

Among the solar cells, dye-sensitized solar cells proposed by Graetzel et al. from Swiss Federal Institute of Technology in Lausanne have been reported to have high photoelectric conversion characteristics greater than or equal to photoelectric conversion characteristics of amorphous silicon solar cells in environments under weak room light (see Panasonic Technical Report, 56 (2008) 87). Room light of, for example, LED lights and fluorescent lamps typically has illuminance of about from 200 Lux through 1,000 Lux, and is light that is by far weaker than direct sunlight (about 100,000 Lux). In many cases, the energy harvesting elements are installed on, for example, walls, but not directly under the room light. In this case, light radiated to the energy harvesting elements becomes even weaker light. Walls in, for example, corridors are at about from 10 Lux through 50 Lux. Hence, a high conversion efficiency is desired even in environments under ultra-weak light.

Structures of the solar cells are formed of: porous metal oxide semiconductors on transparent conductive glass substrates; dyes adsorbed to surfaces of the porous metal oxide semiconductors; electrolytes containing redox couples; and counter electrodes. Graetzel et al. have remarkably improved photoelectric conversion efficiencies by using porous materials as the electrodes formed of the metal oxide semiconductors such as titanium oxide to increase surface areas and by monomolecularly adsorbing ruthenium complexes as the dyes (for example, see Japanese Patent No. 2664194, Nature, 353 (1991) 737, and J. Am. Chem. Soc., 115 (1993) 6382).

Existing dye-sensitized solar cells using electrolytic solutions having high power generation performances are at a risk of, for example, volatilization or leak of the electrolytic solutions. Therefore, for practical use, it is desired to provide the electrolytic solutions in the form of solids. Hitherto, the following solid dye-sensitized solar cells having high power generation performances have been reported.

(1) Solid dye-sensitized solar cells using inorganic semiconductors (for example, see Nature, 485 (2012) 486)

(2) Solid dye-sensitized solar cells using low-molecular-weight organic hole transport materials (for example, see Japanese Unexamined Patent Application Publication No. 11-144773, J. Am. Chem. Soc., 133 (2011) 18042, and J. Am. Chem. Soc., 135 (2013) 7378)

(3) Solid dye-sensitized solar cells using conductive polymers (for example, see Japanese Unexamined Patent Application Publication No. 2000-106223 and J. Phys. Chem. C, 116 (2012) 25721)

The solid dye-sensitized solar cell described in Nature, 485 (2012) 486 and using an inorganic semiconductor in a hole transport layer uses a ruthenium-based dye having a low absorption coefficient. Therefore, there is a need for setting a large titanium oxide film thickness of 6 micrometers or greater. This is accompanied by increase in the number of times of firing the titanium oxide layer and cracking in the titanium oxide layer along with film thickening, resulting in a high production cost.

The solar cell described in J. Am. Chem. Soc., 133 (2011) 18042 is a solid dye-sensitized solar cell using an organic dye having a high absorption coefficient and a spiro-type hole transport material. Using 4-tertial-butylpyridine, this solar cell has a high power generation performance under the sunlight, but a power generation performance of this solar cell under room light has not been reported. It has been reported that when weak light such as room light is converted to electricity, loss current due to an internal resistance in the photoelectric conversion element is considerable (see Fujikura Technical Report, 120 (2011) 42). When the internal resistance is raised, a short-circuiting current density worsens to degrade the photoelectric conversion characteristic. When the internal resistance is lowered, an open circuit voltage worsens to degrade the photoelectric conversion characteristic. That is, it is extremely difficult to satisfy both of: raising the internal resistance; and a good photoelectric conversion characteristic. The open circuit voltage obtained with the photoelectric conversion element is lower under weak room light than under pseudo sunlight. Hence, in order to obtain an output voltage needed for driving an electronic circuit, there is a need for obtaining a high open circuit voltage. Hitherto, there have been reported basic substances that can achieve a high open circuit voltage (see Solar Energy Materials & Solar Cells, 181 (2004) 87).

However, there is no basic material that can achieve a photoelectric conversion characteristic better than hitherto used 4-tertial butylpyridine in a dye-sensitized solar cell of the type using an electrolytic solution such as iodine.

The solar cell described in J. Am. Chem. Soc., 135 (2013) 7378 uses a benzidine-type hole transport material, which can be synthesized at a lower cost than the spiro-type hole transport material used in the solar cell described in J. Am. Chem. Soc., 133 (2011) 18042. Although being a low-cost material, the benzidine-type hole transport material is inferior to the spiro-type hole transport material in the power generation performance.

The solar cell described in J. Phys. Chem. C, 116 (2012) 25721 uses a thiophene-type polymeric material. It is difficult to fill a titanium oxide porous film with a polymeric material. The light absorption wavelength of a thiophene-based polymeric material overlaps the light absorption wavelength of a sensitizing dye. This disturbs the power generation efficiency.

Hence, as for all of the solid photoelectric conversion elements studied so far, only power generation performances under pseudo sunlight have been reported, but power generation performances under room light have not been reported. In Panasonic Technical Report, 56 (2008) 87, environmental testing results have been reported for liquid dye-sensitized solar cells, but not for solid dye-sensitized solar cells.

SUMMARY OF THE INVENTION

According to one aspect of the present disclosure, a photoelectric conversion element includes a first electrode, a hole blocking layer, an electron transport layer, a hole transport layer, and a second electrode. The hole transport layer contains a compound represented by general formula (1) below.

(In the formula, $R_1$ represents a methoxy group or an ethoxy group, $R_2$ represents a hydrogen group or a methyl group, $R_3$ represents a hydrogen group, a methyl group, or a methoxy group, $R_4$ represents a methoxy group, and X represents —$CH_2$—, —$CH_2CH_2$—, —O—, or —$C(CH_2)_5$—.)

DESCRIPTION OF THE EMBODIMENTS

Figure 1:
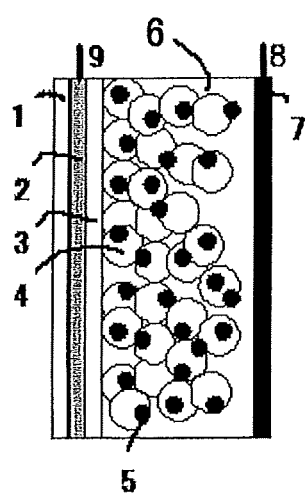
FIG. 1 is a schematic exemplary view illustrating an example of a structure of a photoelectric conversion element according to the present disclosure.

Hence, the present disclosure has an object to provide a photoelectric conversion element that can obtain a good photoelectric conversion characteristic even under weak irradiation light such as room light.

The present disclosure can provide a photoelectric conversion element that can obtain a good photoelectric conversion characteristic even under weak irradiation light such as room light.

A photoelectric conversion element according to the present disclosure will be described below with reference to the drawing. The present disclosure is not limited to the embodiment described below, but other embodiments, additions, modifications, deletions, etc. may be made within a conceivable scope of persons skilled in the art. Any embodiments that have the working and effects of the present disclosure are intended to be included within the scope of the present disclosure.

The photoelectric conversion element of the present disclosure includes a first electrode, a hole blocking layer, an

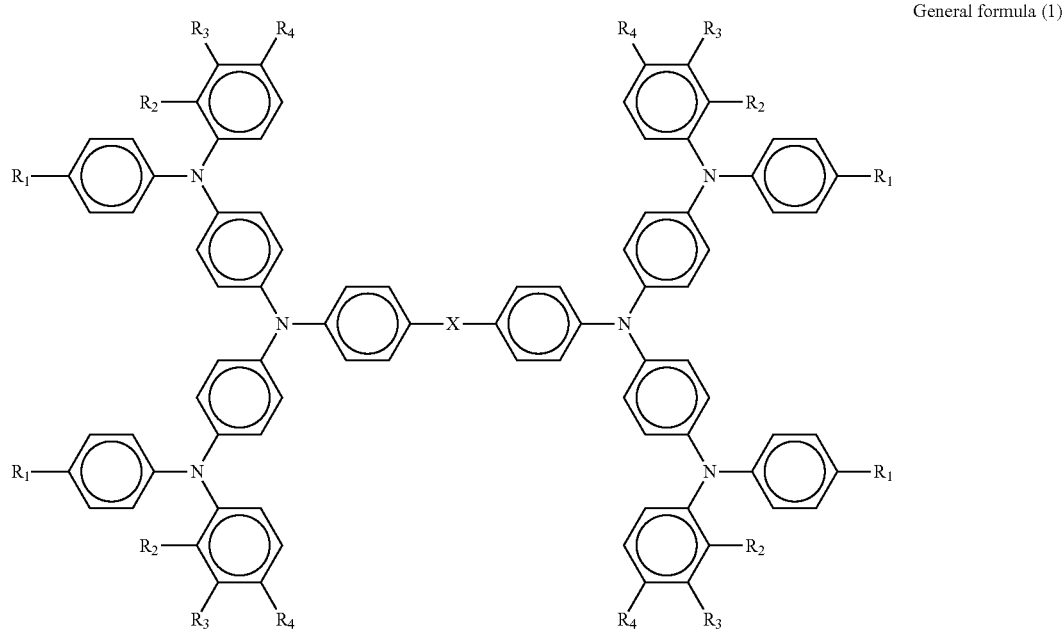

General formula (1)

electron transport layer, a hole transport layer, and a second electrode. The hole transport layer contains a compound represented by general formula (1) below.

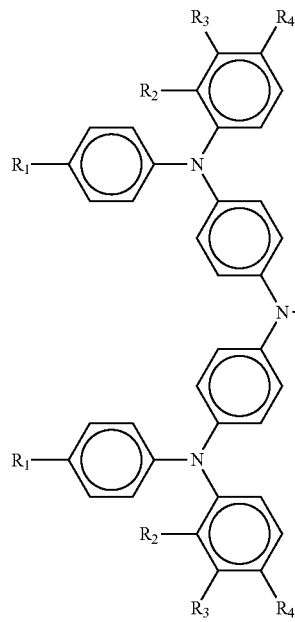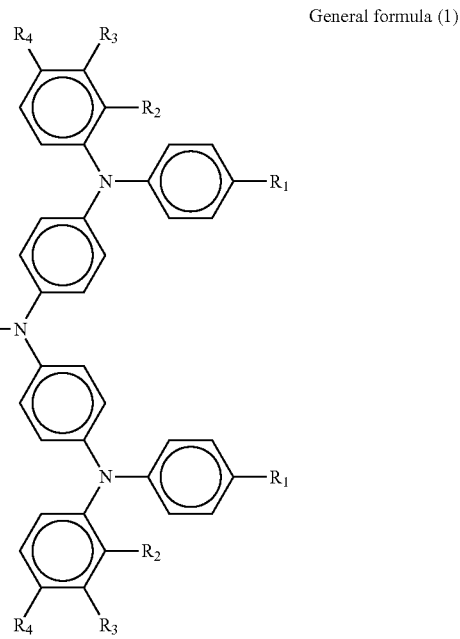

General formula (1)

(In the formula, $R_1$ represents a methoxy group or an ethoxy group, $R_2$ represents a hydrogen group or a methyl group, $R_3$ represents a hydrogen group, a methyl group, or a methoxy group, $R_4$ represents a methoxy group, and X represents —$CH_2$—, —$CH_2CH_2$—, —O—, or —C($CH_2$)$_5$—.)

According to the present disclosure, a good photoelectric conversion characteristic can be obtained even under weak irradiation light such as room light of, for example, about from 10 Lux through 50 Lux. In the present disclosure, a photoelectric conversion element refers to an element configured to convert light energy to electric energy or an element configured to convert electric energy to light energy. Specific examples include solar cells and photodiodes. The photoelectric conversion element of the present disclosure can be used as, for example, a solar cell and a photodiode.

The configuration of the photoelectric conversion element will be described based on FIG. 1. FIG. 1 is a view exemplarily illustrating a cross-section of an example of the photoelectric conversion element according to the present disclosure.

The embodiment illustrated in FIG. 1 is a configuration example in which a first electrode 2 is formed on a substrate 1, a hole blocking layer 3 is formed on the first electrode 2, an electron transport layer 4 is formed on the hole blocking layer 3, a photosensitizing compound 5 is adsorbed to the electron transport material in the electron transport layer 4, and a hole transport layer 6 is interposed between the first electrode 2 and a second electrode 7 counter to the first electrode 2. The configuration example illustrated in FIG. 1 also includes lead lines 8 and 9 provided in a manner to make the first electrode 2 and the second electrode 7 electrically continuous. Details will be described below.

<Substrate>

The substrate 1 used in the present disclosure is not particularly limited and a known substrate may be used. It is preferable that the substrate 1 be formed of a transparent material. Examples of the material include glass, transparent plastic plates, transparent plastic films, and inorganic transparent crystal substances.

<First Electrode>

The first electrode 2 used in the present disclosure is not particularly limited so long as the first electrode 2 is a conductive substance transparent to visible light. It is possible to use known conductive materials used in, for example, typical photoelectric conversion elements or liquid crystal panels.

Examples of the material of the first electrode include indium tin oxide (hereinafter referred to as ITO), fluorine-doped tin oxide (hereinafter referred to as FTO), antimony-doped tin oxide (hereinafter referred to as ATO), indium-zinc oxide, niobium-titanium oxide, and graphene. One of these materials may be used alone or two or more of these materials may be laminated.

A thickness of the first electrode is preferably from 5 nm through 10 micrometers and more preferably from 50 nm through 1 micrometer.

It is preferable that the first electrode be provided on the substrate 1 formed of a material transparent to visible light, in order to maintain a constant hardness. For example, glass, a transparent plastic plate, a transparent plastic film, or an inorganic transparent crystalline substance is used for the substrate.

It is also possible to use a known integrated body of the first electrode and the substrate. Examples of the integrated body include FTO-coated glass, ITO-coated glass, zinc oxide: aluminum-coated glass, a FTO-coated transparent plastic film, and an ITO-coated transparent plastic film.

It is also possible to use a product in which a transparent electrode of tin oxide or indium oxide doped with a cation or an anion different in valence or a metal electrode formed into a light-transmissive structure such as a mesh form and a stripe form is provided on a substrate such as a glass substrate.

One of these materials may be used alone or two or more of these materials may be mixed together or laminated. Furthermore, with a view to lowering a resistance, for example, a metal lead line may be used in combination.

Examples of the material of the metal lead line include metals such as aluminum, copper, silver, gold, platinum, and nickel. The metal lead line can be formed by a method of locating the metal lead line on the substrate by, for example, vapor deposition, sputtering, or pressure bonding and providing the ITO or the FTO on the metal lead line.

<Hole Blocking Layer>

The hole blocking layer 3 used in the present disclosure is not particularly limited so long as the hole blocking layer 3 is transparent to visible light and is an electron transport material. However, titanium oxide is particularly preferable as the hole blocking layer 3. The hole blocking layer 3 is provided in order to suppress a fall in electric power due to contact of an electrolyte with an electrode and consequent recombination between holes in the electrolyte and electrons in a surface of the electrode (so-called back electron transfer). This effect of the hole blocking layer 3 is particularly remarkable in solid dye-sensitized solar cells. This is because a speed of recombination (back electron transfer) between holes in hole transport materials and electrons in surfaces of electrodes is higher in solid dye-sensitized solar cells using, for example, organic hole transport materials than in wet dye-sensitized solar cells using electrolytic solutions.

A film forming method for the hole blocking layer is not particularly limited. However, in order to suppress loss current under room light, a high internal resistance is needed, and a film forming method matters. Examples of typical methods include a sol-gel method, which is wet film formation, which however results in a low film density to make it impossible to suppress loss current sufficiently. Hence, dry film formation such as a sputtering method is more preferable because a sufficiently high film density is obtained to make it possible to suppress loss current.

The hole blocking layer is formed also with a view to preventing an electronic contact between the first electrode 2 and the hole transport layer 6. A thickness of the hole blocking layer is not particularly limited but is preferably from 5 nm through 1 micrometer, more preferably from 500 nm through 700 nm in wet film formation, and more preferably from 10 nm through 30 nm in dry film formation.

<Electron Transport Layer>

The photoelectric conversion element of the present disclosure includes a porous electron transport layer 4 on the hole blocking layer 3. It is preferable that the electron transport layer contain an electron transport material such as semiconductor particles. The electron transport layer 4 may contain a single layer or multiple layers. In the case of the multiple layers, it is possible to form multiple layers by coating dispersion liquids of semiconductor particles having different particle diameters, or it is also possible to form multiple layers by coating different kinds of semiconductors or different resin or additive compositions. When a sufficient thickness is not obtained with one coating, the coating of multiple layers is an effective means.

Typically, an amount of a photosensitizing material (photosensitizing compound) supported by the electron transport layer per a unit projected area increases as a thickness of the electron transport layer is increased, leading to an increase in a light capture rate. However, this also increases a distance to which injected electrons diffuse, to increase loss due to recombination of charges. Hence, the thickness of the electron transport layer is preferably from 100 nm through 100 micrometers.

The semiconductor is not particularly limited and a known semiconductor may be used.

Specific examples of the semiconductor include element semiconductors such as silicon and germanium, compound semiconductors represented by chalcogenides of metals, and compounds having a perovskite structure.

Examples of the chalcogenides of metals include: oxides of titanium, tin, zinc, iron, tungsten, zirconium, hafnium, strontium, indium, cerium, yttrium, lanthanum, vanadium, niobium, and tantalum; sulfides of cadmium, zinc, lead, silver, antimony, and bismuth; selenides of cadmium and lead; and telluride of cadmium.

Examples of other compound semiconductors include: phosphides of, for example, zinc, gallium, indium, and cadmium; gallium arsenide; copper-indium-selenide; and copper-indium-sulfide.

Examples of the compounds having a perovskite structure include strontium titanate, calcium titanate, sodium titanate, barium titanate, and potassium niobate.

Among these semiconductors, oxide semiconductors are preferable, and titanium oxide, zinc oxide, tin oxide, and niobium oxide are particularly preferable. One of these semiconductors may be used alone or two or more of these semiconductors may be used as a mixture. A crystal form of these semiconductors is not particularly limited and may be monocrystalline, polycrystalline, or amorphous.

A size of the semiconductor particles is not particularly limited. However, an average primary particle diameter is preferably from 1 nm through 100 nm and more preferably from 5 nm through 50 nm.

It is also possible to improve efficiency based on an incident-light-scattering effect obtained by mixing or laminating semiconductor particles having a greater average particle diameter. In this case, an average particle diameter of the semiconductor is preferably from 50 nm through 500 nm.

A method for producing the electron transport layer is not particularly limited. Examples of the method include a method for forming a thin film in vacuum, such as sputtering, and a wet film forming method. When production costs and other factors are taken into consideration, the wet film forming method is preferable, and a method of preparing a paste in which powder or sol of the semiconductor particles is dispersed, and coating the hole blocking layer over an electron collecting electrode (first electrode) substrate with the paste is preferable.

In using the wet film forming method, a coating method is not particularly limited and may be performed according to a known method.

For example, it is possible to use a dipping method, a spraying method, a wire bar method, a spin coating method, a roller coating method, a blade coating method, and a gravure coating method, and wet printing methods including various methods such as letterpress, offset, gravure, intaglio, rubber plate, and screen printing.

In producing a dispersion liquid of the semiconductor particles by mechanical pulverization or using a mill, the dispersion liquid is formed by dispersing at least the semiconductor particles alone or a mixture of the semiconductor particles and a resin in water or an organic solvent.

Examples of the resin to be used here include polymers or copolymers of vinyl compounds based on, for example, styrene, vinyl acetate, acrylic acid ester, and methacrylic acid ester, silicon resins, phenoxy resins, polysulfone resins, polyvinyl butyral resins, polyvinyl formal resins, polyester resins, cellulose ester resins, cellulose ether resins, urethane resins, phenol resins, epoxy resins, polycarbonate resins, polyarylate resins, polyamide resins, and polyimide resins.

Examples of the solvent in which the semiconductor particles are dispersed include water; alcohol-based solvents such as methanol, ethanol, isopropyl alcohol, and α-terpineol; ketone-based solvents such as acetone, methyl ethyl ketone, and methyl isobutyl ketone; ester-based solvents such as ethyl formate, ethyl acetate, and n-butyl acetate; ether-based solvents such as diethyl ether, dimethoxyethane, tetrahydrofuran, dioxolane, and dioxane; amide-based solvents such as N,N-dimethylformamide, N,N-dimethylacetamide, and N-methyl-2-pyrrolidone; halogenated hydrocarbon-based solvents such as dichloromethane, chloroform, bromoform, methyl iodide, dichloroethane, trichloroethane, trichloroethylene, chlorobenzene, o-dichlorobenzene, fluorobenzene, bromobenzene, iodobenzene, and 1-chloronaphthalene; and hydrocarbon-based solvents such as n-pentane, n-hexane, n-octane, 1,5-hexadiene, cyclohexane, methylcyclohexane, cyclohexadiene, benzene, toluene, o-xylene, m-xylene, p-xylene, ethylbenzene, and cumene. One of these solvents may be used alone or two or more of these solvents may be used as a mixture solvent.

For prevention of reaggregation of particles, for example, an acid such as hydrochloric acid, nitric acid, and acetic acid, a surfactant such as polyoxyethylene (10) octylphenyl ether, and a chelate agent such as acetylacetone, 2-aminoethanol, and ethylene diamine may be added to the dispersion liquid of the semiconductor particles or to the paste of the semiconductor particles obtained by, for example, a sol-gel method.

Furthermore, adding a thickener with a view to improving a film forming property is an effective means.

Examples of the thickener to be added here include polymers such as polyethylene glycols and polyvinyl alcohols and thickeners such as ethyl cellulose.

It is preferable to subject the semiconductor particles after coated to firing, microwave irradiation, electron beam irradiation, or laser light irradiation in order to provide an electronic contact between the particles, improve a film strength, and improve close adhesiveness with the substrate. These treatments may be applied alone or two or more kinds of these treatments may be applied in combination.

In the firing, a firing temperature is not limited to a particular range, but is preferably from 30 degrees C. through 700 degrees C. and more preferably from 100 degrees C. through 600 degrees C. because the resistance of the substrate may rise or the substrate may melt if the temperature is excessively high. A firing time is also not particularly limited, but is preferably from 10 minutes through 10 hours.

The microwave irradiation may be given from a side at which the electron transport layer is formed or from a back side.

An irradiation time is not particularly limited, but is preferably within 1 hour.

After firing, for example, chemical plating using an aqueous solution of titanium tetrachloride or a mixture solution of titanium tetrachloride with an organic solvent or an electrochemical plating treatment using a titanium trichloride aqueous solution may be performed with a view to increasing a surface area of the semiconductor particles and increasing efficiency of electron injection from the photosensitizing compound into the semiconductor particles.

A porous state is formed in the film obtained by depositing the semiconductor particles having a diameter of several tens of nanometers by, for example, sintering. This nanoporous structure has an extremely large surface area. The surface area can be expressed by a roughness factor.

The roughness factor is a value representing an actual area inside the porous texture relative to an area of the semiconductor particles coated on the substrate. Hence, a greater roughness factor is more preferable. However, considering the relationship with the film thickness of the electron transport layer, the roughness factor is preferably 20 or greater in the present disclosure.

<Photosensitizing Compound>

In the present disclosure, in order to further improve the conversion efficiency, it is preferable to adsorb a photosensitizing compound to a surface of the electron transport semiconductor (electron transport material), which is the electron transport layer 4.

The photosensitizing compound 5 is not particularly limited to the above so long as the photosensitizing compound 5 is a compound optically excitable by excitation light used. Specific examples of the photosensitizing compound 5 also include the following compounds.

Specific examples of the photosensitizing compound include: metal complex compounds described in, e.g., Japanese Translation of PCT International Application Publication No. JP-T-07-500630, and Japanese Unexamined Patent Application Publication Nos. 10-233238, 2000-26487, 2000-323191, and 2001-59062; coumarin compounds described in, e.g., Japanese Unexamined Patent Application Publication Nos. 10-93118, 2002-164089, and 2004-95450, and J. Phys. Chem. C, 7224, Vol. 111 (2007); polyene compounds described in, e.g., Japanese Unexamined Patent Application Publication No. 2004-95450 and Chem. Commun., 4887 (2007); indoline compounds described in, e.g., Japanese Unexamined Patent Application Publication Nos. 2003-264010, 2004-63274, 2004-115636, 2004-200068, and 2004-235052, J. Am. Chem. Soc., 12218, Vol. 126 (2004), Chem. Commun., 3036 (2003), and Angew. Chem. Int. Ed., 1923, Vol. 47 (2008); thiophene compounds described in, e.g., J. Am. Chem. Soc., 16701, Vol. 128 (2006), and J. Am. Chem. Soc., 14256, Vol. 128 (2006); cyanine dyes described in, e.g., Japanese Unexamined Patent Application Publication Nos. 11-86916, 11-214730, 2000-106224, 2001-76773, and 2003-7359; merocyanine dyes described in, e.g., Japanese Unexamined Patent Application Publication Nos. 11-214731, 11-238905, 2001-52766, 2001-76775, and 2003-7360; 9-arylxanthene compounds described in, e.g., Japanese Unexamined Patent Application Publication Nos. 10-92477, 11-273754, 11-273755, and 2003-31273; triarylmethane compounds described in, e.g., Japanese Unexamined Patent Application Publication Nos. 10-93118 and 2003-31273; and phthalocyanine compounds and porphyrin compounds described in, e.g., Japanese Unexamined Patent Application Publication Nos. 09-199744, 10-233238, 11-204821, and 11-265738, J. Phys. Chem., 2342, Vol. 91 (1987), J. Phys. Chem. B, 6272, Vol. 97 (1993), Electroanal. Chem., 31, Vol. 537 (2002), Japanese Unexamined Patent Application Publication No. 2006-032260, J. Porphyrins Phthalocyanines, 230, Vol. 3(1999), Angew. Chem. Int. Ed., 373, Vol. 46 (2007), and Langmuir, 5436, Vol. 24 (2008). Among these photosensitizing compounds, the metal complex compounds, the coumarin compounds, the polyene compounds, the indoline compounds, and the thiophene compounds are particularly preferable. More preferable examples of the photosensitizing compound include D131 represented by structural formula (4) below, D102 represented by structural formula (5) below, and D358 represented by structural formula (6) below, all available from Mitsubishi Paper Mills Limited.

Structural formula (4)

(D131)

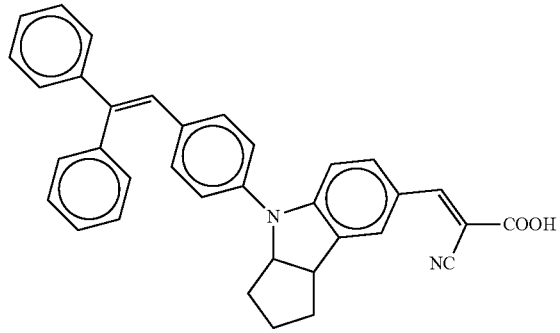

Structural formula (5)

(D102)

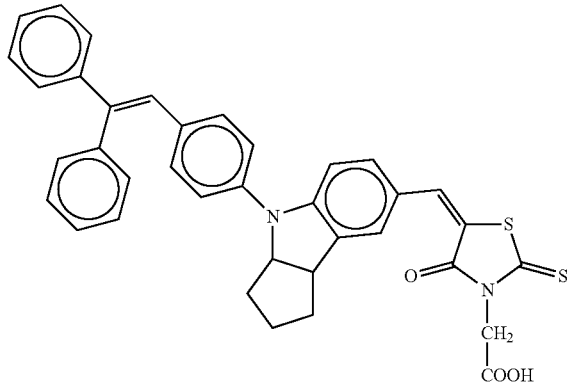

Structural formula (6)

(D358)

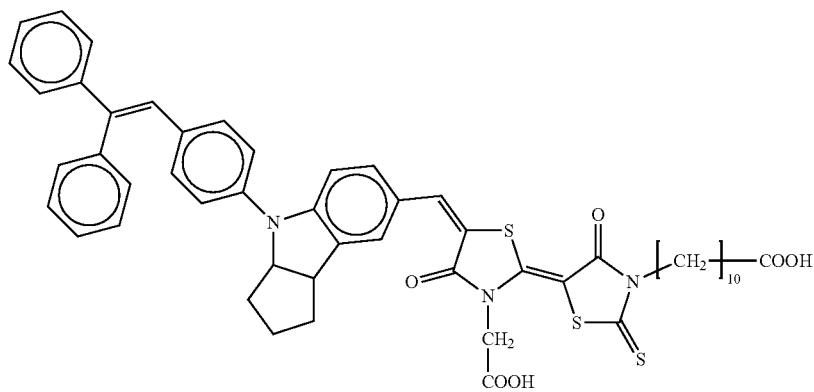

As a method for adsorbing the photosensitizing compound 5 to the electron transport layer 4, it is possible to use a method of immersing the electron collecting electrode (first electrode) containing the semiconductor particles in a photosensitizing compound solution or dispersion liquid and a method of coating the electron transport layer with the solution or the dispersion liquid to adsorb the photosensitizing compound.

As the former method, for example, an immersing method, a dipping method, a roller method, and an air knife method may be used.

As the latter method, for example, a wire bar method, a slide hopper method, an extrusion method, a curtain method, a spinning method, and a spraying method may be used.

The photosensitizing compound may be adsorbed under a supercritical fluid using, for example, carbon dioxide.

In adsorbing the photosensitizing compound, a condensing agent may be used in combination.

The condensing agent may be any of: a substance that is assumed to catalyze physical or chemical binding of the photosensitizing material and the electron transport compound with a surface of an inorganic substance; and a substance that acts stoichiometrically to cause a chemical equilibrium to move in an advantageous manner.

Furthermore, thiol or a hydroxy compound may be added as a condensing aid.

Examples of a solvent in which the photosensitizing compound is dissolved or dispersed include:

water;

alcohol-based solvents such as methanol, ethanol, and isopropyl alcohol;

ketone-based solvents such as acetone, methyl ethyl ketone, and methyl isobutyl ketone;

ester-based solvents such as ethyl formate, ethyl acetate, and n-butyl acetate;

ether-based solvents such as diethyl ether, dimethoxyethane, tetrahydrofuran, dioxolane, and dioxane;

amide-based solvents such as N,N-dimethylformamide, N,N-dimethylacetamide, and N-methyl-2-pyrrolidone;

halogenated hydrocarbon-based solvents such as dichloromethane, chloroform, bromoform, methyl iodide, dichloroethane, trichloroethane, trichloroethylene, chlorobenzene, o-dichlorobenzene, fluorobenzene, bromobenzene, iodobenzene, and 1-chloronaphthalene; and hydrocarbon-based solvents such as n-pentane, n-hexane, n-octane, 1,5-hexadiene, cyclohexane, methylcyclohexane, cyclohexadiene, benzene, toluene, o-xylene, m-xylene, p-xylene, ethylbenzene, and cumene. One of these solvents may be used alone or two or more of these solvents may be used as a mixture.

Some kinds of the photosensitizing compounds act more effectively when aggregation between different compounds is suppressed. Hence, a deaggregating agent may be used in combination.

As the deaggregating agent, steroid compounds such as cholic acid and chenodeoxycholic acid, long-chain alkylcarboxylic acids, or long-chain alkylphosphonic acids are preferable. An appropriate deaggregating agent is selected depending on the dye used.

An amount of the deaggregating agent added is preferably from 0.01 parts by mass through 500 parts by mass and more preferably from 0.1 parts by mass through 100 parts by mass relative to 1 part by mass of the photosensitizing compound.

A temperature in using these materials and adsorbing the photosensitizing compound and the deaggregating agent to the electron transport layer 4 is preferably −50 degrees C. or higher but 200 degrees C. or lower.

The adsorption may be performed in a still state or under stirring.

Examples of the method for the stirring include, but are not limited to: a stirrer, a ball mill, a paint conditioner, a sand mill, an attritor, a disperser, and ultrasonic dispersion.

A time needed for the adsorption is preferably 5 seconds or longer but 1,000 hours or shorter, more preferably 10 seconds or longer but 500 hours or shorter, and yet more preferably 1 minute or longer but 150 hours or shorter.

Furthermore, it is preferable to perform the adsorption in a dark place.

<Hole Transport Layer>

As a typical hole transport layer, for example, an electrolytic solution obtained by dissolving a redox couple in an organic solvent, a gel electrolyte obtained by immersing in a polymer matrix, a liquid obtained by dissolving a redox couple in an organic solvent, a molten salt containing a redox couple, a solid electrolyte, an inorganic hole transport material, and an organic hole transport material are used. The hole transport layer 6 of the present disclosure contains an organic hole transport material such as a compound represented by general formula (1) above. Specific exemplary compounds of general formula (1) above are presented below.

Compound No. 1-1

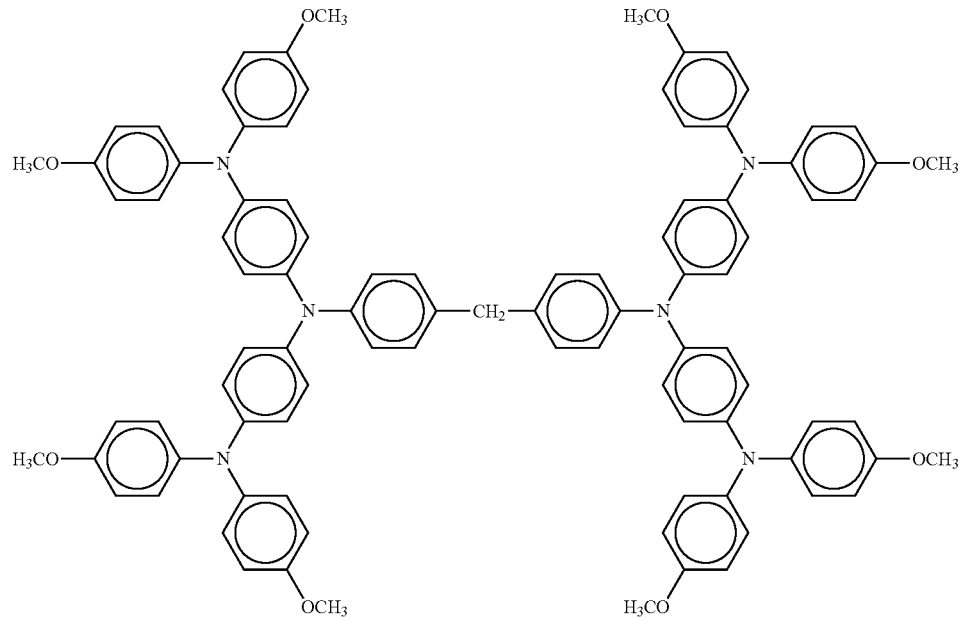

Compound No. 1-2
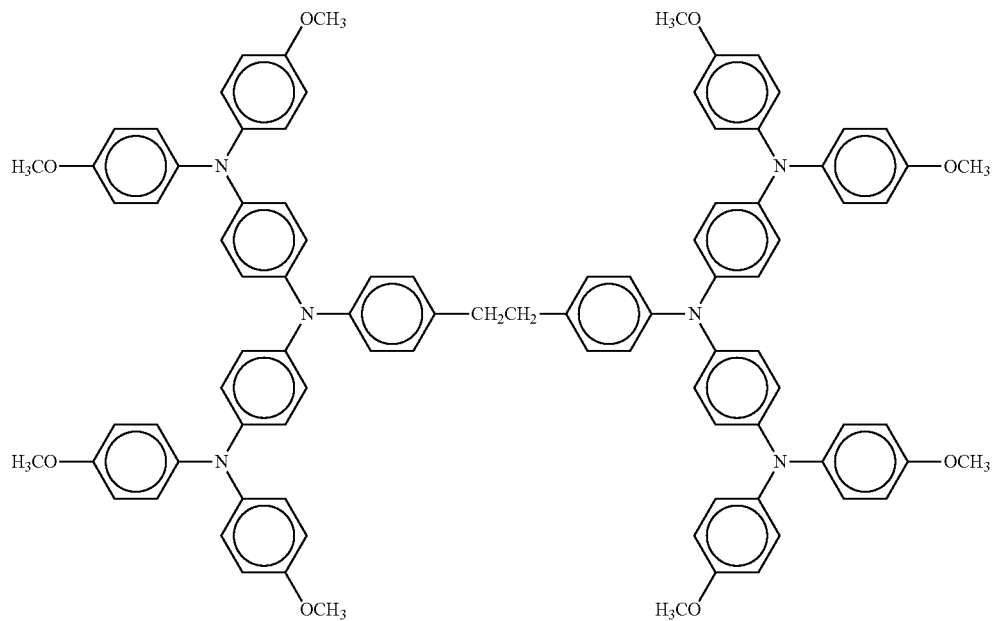
Compound No. 1-3
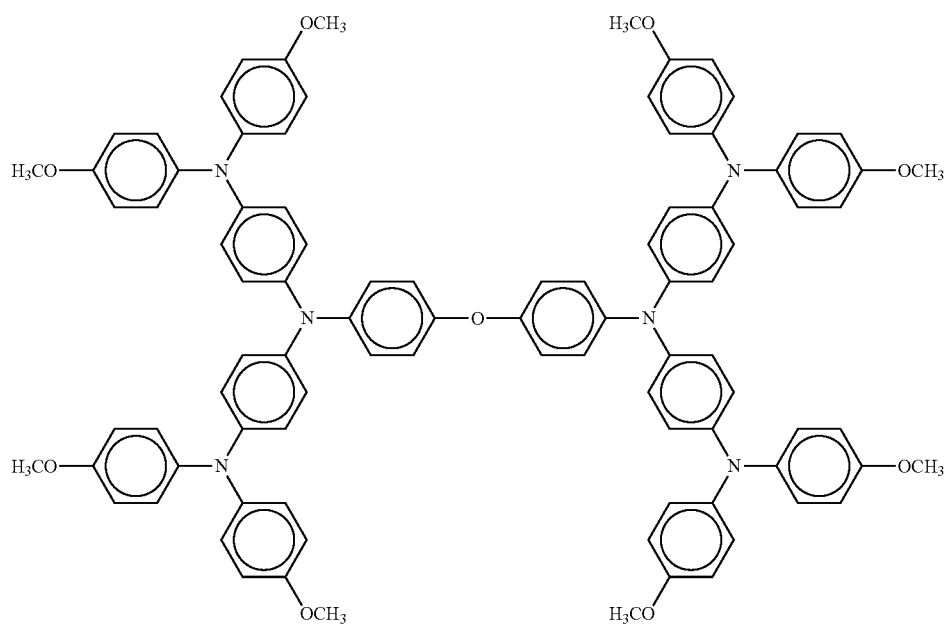

Compound No. 1-4
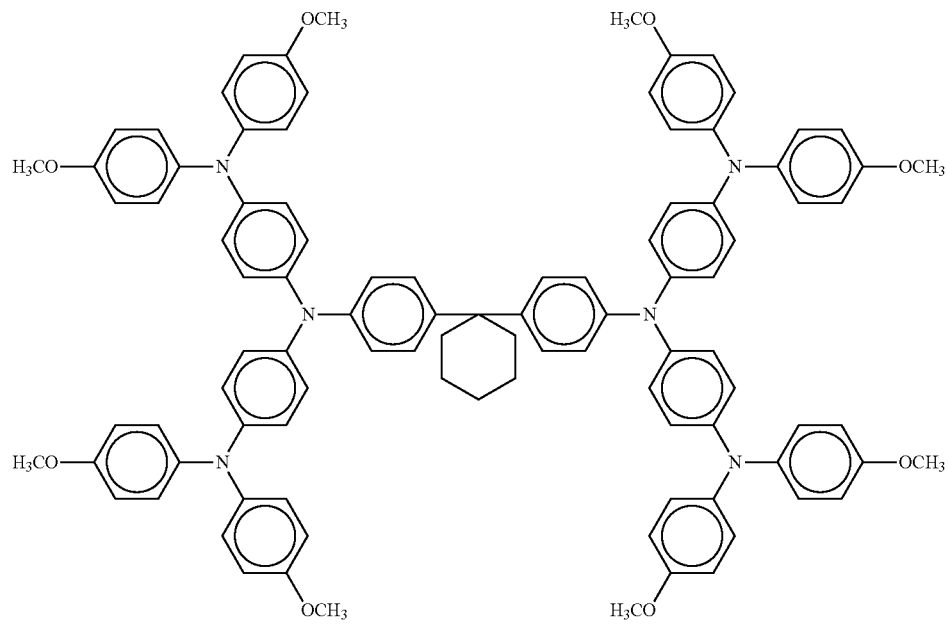
Compound No. 1-5
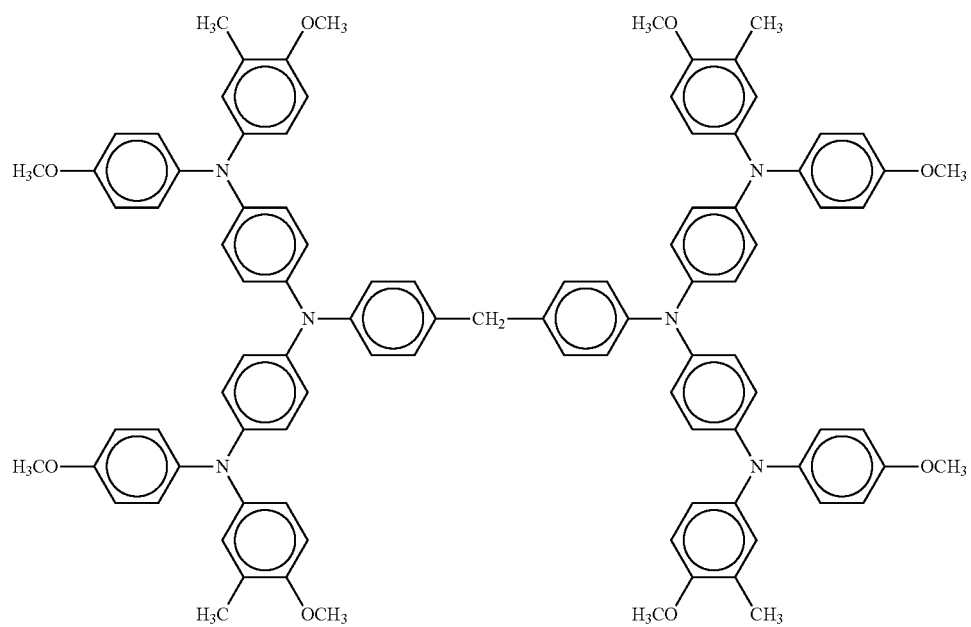

Compound No. 1-6
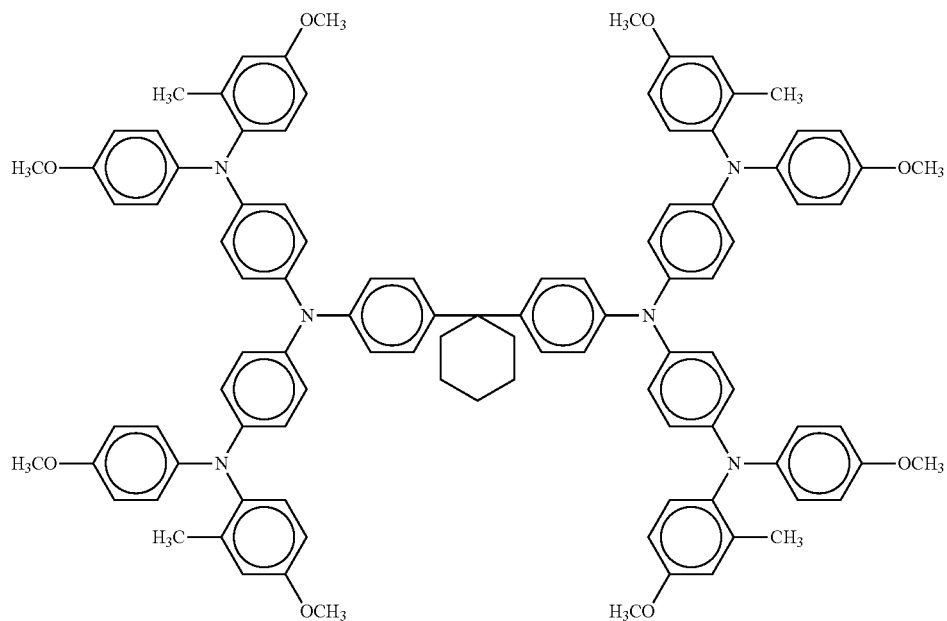
Compound No. 1-7
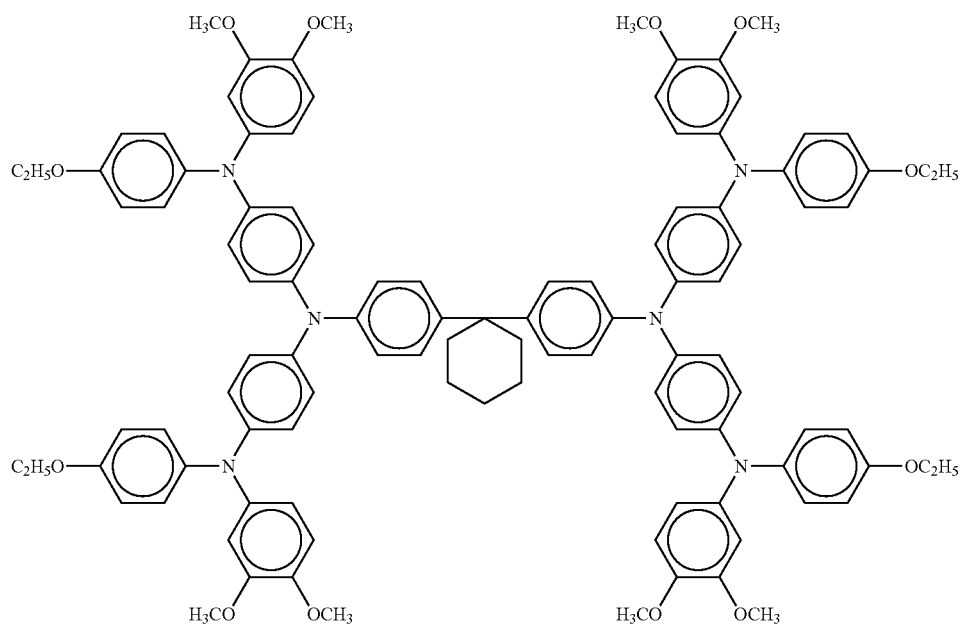

It is preferable that the hole transport layer 6 of the present disclosure contain an organic hole transport material such as a compound represented by general formula (2) below.

General formula (2)

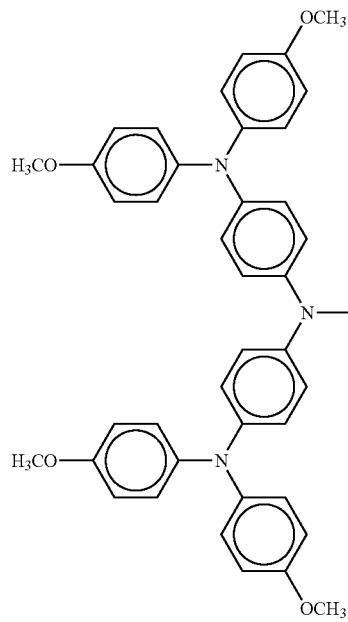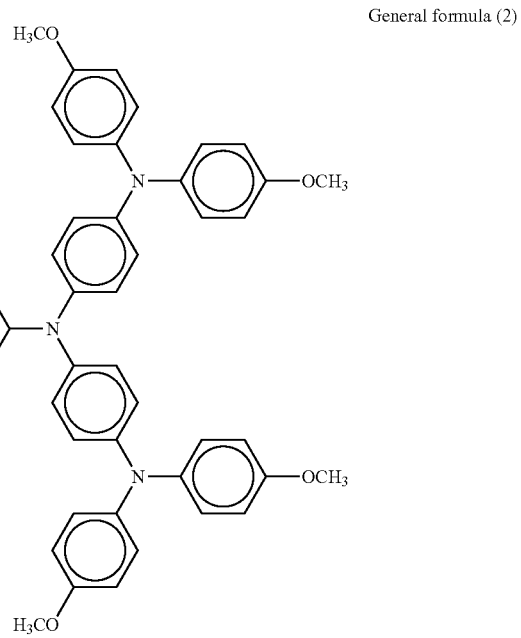

(In the formula, X represents —$CH_2$—, —$CH_2CH_2$—, —O—, or —$C(CH_2)_5$—.)

It is preferable that the content of the compound represented by general formula (1) above in the hole transport layer be from 40% by mass through 90% by mass.

The hole transport layer 6 of the present disclosure may have a single-layer structure or a laminated structure formed of different compounds. In the case of the laminated structure, it is preferable to use a polymer material in the hole transport layer 6 near the second electrode 7.

This is because use of a polymer material having an excellent film forming property in the hole transport layer 6 can make the surface of the porous electron transport layer smoother and can improve the photoelectric conversion characteristic.

Furthermore, it is difficult for a polymer material to permeate the inside of the porous electron transport layer. This in turns makes the polymer material excellent in coating the surface of the porous electron transport layer and effective for preventing short circuiting when an electrode is provided, leading to a higher performance.

An organic hole transport material used in a single-layer structure may be the compound represented by general formula (1) above, or may be a known organic hole transport compound.

Specific examples of the known organic hole transport compound include: oxadiazole compounds presented in, e.g., Japanese Examined Patent Publication No. 34-5466; triphenylmethane compounds presented in, e.g., Japanese Examined Patent Publication No. 45-555; pyrazoline compounds presented in, e.g., Japanese Examined Patent Publication No. 52-4188; hydrazone compounds presented in, e.g., Japanese Examined Patent Publication No. 55-42380; oxadiazole compounds presented in, e.g., Japanese Unexamined Patent Application Publication No. 56-123544; tetraarylbenzidine compounds presented in Japanese Unexamined Patent Application Publication No. 54-58445; and stilbene compounds presented in Japanese Unexamined Patent Application Publication No. 58-65440 or Japanese Unexamined Patent Application Publication No. 60-98437.

J. Am. Chem. Soc., 133 (2011) 18042 describes 2,2',7,7'-tetrakis(N,N-di-p-methoxyphenylamino)-9,9'-spirobifluorene, and J. Am. Chem. Soc., 135 (2013) 7378 describes N,N,N',N'-tetrakis(4-methoxyphenyl)benzidine, which is described as exhibiting an excellent photoelectric conversion characteristic.

When the hole transport layer 6 has a laminated structure, a polymer material is preferable as an organic hole transport material near the second electrode 7 as described above. A known hole transportable polymer material may be used as the polymer material.

Specific examples of the known hole transportable polymer material include:

polythiophene compounds such as poly(3-n-hexylthiophene), poly(3-n-octyloxythiophene), poly(9,9'-dioctylfluorene-co-bithiophene), poly(3,3'''-didodecyl-quarter thiophene), poly(3,6-dioctylthieno[3,2-b]thiophene), poly(2,5-bis(3-decylthiophen-2-yl)thieno[3,2-b]thiophene), poly(3,4-didecylthiophene-co-thieno[3,2-b]thiophene), poly(3,6-dioctylthieno[3,2-b]thiophene-co-thieno[3,2-b]thiophene), poly(3,6-dioctylthieno[3,2-b]thiophene-co-thiophene), and poly(3,6-dioctylthieno[3,2-b]thiophene-co-bithiophene);

polyphenylenevinylene compounds such as poly[2-methoxy-5-(2-ethylhexyloxy)-1,4-phenylenevinylene], poly[2-methoxy-5-(3,7-dimethyloctyloxy)-1,4-phenylenevinylene], and poly[(2-methoxy-5-(2-ethylphexyloxy)-1,4-phenylenevinylene)-co-(4,4'-biphenylene-vinylene)];

polyfluorene compounds such as poly(9,9'-didodecylfluorenyl-2,7-diyl), poly[(9,9-dioctyl-2,7-divinylenefluorene)-alt-co-(9,10-anthracene)], poly[(9,9-dioctyl-2,7-divinylenefluorene)-alt-co-(4,4'-biphenylene)], poly[(9,9-dioctyl-2,7-divinylenefluorene)-alt-co-(2-methoxy-5-(2-ethylhexyloxy)-1,4-phenylene)], and poly[(9,9-dioctyl-2,7-diyl)-co-(1,4-(2,5-dihexyloxy)benzene)];

polyphenylene compounds such as poly[2,5-dioctyloxy-1,4-phenylene] and poly[2,5-di(2-ethylhexyloxy-1,4-phenylene];

polyarylamine compounds such as poly[(9,9-dioctylfluorenyl-2,7-diyl)-alt-co-(N,N'-diphenyl)-N,N'-di(p-hexylphenyl)-1,4-diaminobenzene], poly[(9,9-dioctylfluorenyl-2,7-diyl)-alt-co-(N,N'-bis(4-octyloxyphenyl)benzidine-N,N'-(1,4-diphenylene)], poly[(N,N'-bis(4-octyloxyphenyl)benzidine-N,N'-(1,4-diphenylene)], poly[(N,N'-bis(4-(2-ethylhexyloxy)phenyl)benzidine-N,N'-(1,4-diphenylene)], poly[phenylimino-1,4-phenylenevinylene-2,5-dioctyloxy-1,4-phenylenevinylene-1,4-phenylene], poly[p-tolylimino-1,4-phenylenevinylene-2,5-di(2-ethylhexyloxy)-1,4-phenylenevinylene-1,4-phenylene], and poly[4-(2-ethylhexyloxy)phenylimino-1,4-biphenylene]; and polythiadiazole compounds such as poly[(9,9-dioctylfluorenyl-2,7-diyl)-alt-co-(1,4-benzo(2,1',3)thiadiazole] and poly(3,4-didecylthiophene-co-(1,4-benzo(2,1',3)thiadiazole).

Among these hole transportable polymer materials, the polythiophene compounds and the polyarylamine compounds are particularly preferable, considering carrier mobility and ionization potential.

Various additives may be added in the organic hole transport material presented above.

Examples of the additives include:

iodine;

metal iodides such as lithium iodide, sodium iodide, potassium iodide, cesium iodide, calcium iodide, copper iodide, iron iodide, and silver iodide;

quaternary ammonium salts such as tetraalkylammonium iodide and pyridinium iodide;

metal bromides such as lithium bromide, sodium bromide, potassium bromide, cesium bromide, and calcium bromide;

bromine salts of quaternary ammonium compounds, such as tetraalkylammonium bromide and pyridinium bromide;

metal chlorides such as copper chloride and silver chloride; metal acetates such as copper acetate, silver acetate, and palladium acetate;

metal sulfates such as copper sulfate and zinc sulfate; metal complexes such as ferrocyanate-ferricyanate and ferrocene-ferricinium ion;

sulfur compounds such as polysodium sulfide and alkylthiol-alkyldisulfide;

viologen dyes, hydroquinone, etc.; ionic liquids described in Inorg. Chem. 35 (1996) 1168, such as 1,2-dimethyl-3-n-propylimidazolinium iodide, 1-methyl-3-n-hexylimidazolinium iodide, 1,2-dimethyl-3-ethylimidazoliumtrifluoromethane sulfonic acid salt, 1-methyl-3-butylimidazoliumnonafluorobutyl sulfonic acid salt, 1-methyl-3-ethylimidazoliumbis(trifluoromethyl)sulfonylimide, and 1-n-hexyl-3-methylimidazoliniumbis(trifluoromethylsulfonyl)imide; basic compounds such as pyridine, 4-t-butylpyridine, and benzimidazole; and lithium compounds such as lithium trifluoromethane sulfonylimide, lithium bistrifluoromethane sulfonylimide, and lithium diisopropylimide.

Among these additives, imidazolium compounds among the ionic liquids are preferable. It is preferable to use the compound at a ratio of from 1% by mass through 10% by mass relative to the organic hole transport material.

In the present disclosure, addition of a basic compound represented by general formula (3) below in the hole transport layer 6 makes it possible to obtain a particularly high open circuit voltage.

Moreover, addition of this basic compound makes it possible to raise the internal resistance in the photoelectric conversion element and reduce loss current under weak light such as room light. Hence, this basic compound can obtain a higher open circuit voltage than obtained with existing basic compounds.

General formula (3)

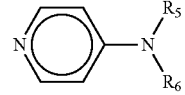

(In the formula, $R_5$ and $R_6$ represent a substituted or unsubstituted alkyl group or aromatic hydrocarbon group, and may be the same as or different from each other. $R_5$ and $R_6$ may bind with each other to form a substituted or unsubstituted heterocyclic group containing a nitrogen atom.)

Hitherto, there have been known compounds that have a similar structure to general formula (3) above and are classified into the basic compounds presented below. Some of these compounds are known to have been used as basic compounds in iodine electrolytic solution-type dye-sensitized solar cells. These compounds provide a high open circuit voltage, but have been reported to significantly reduce a short-circuiting current density and considerably worsen a photoelectric conversion characteristic.

The hole transport layer of the present disclosure uses an organic hole transport material and is different from a hole transport model based on, for example, the iodine electrolytic solution mentioned above. Hence, reduction of a short-circuiting current density is low and a high open circuit voltage can be obtained, to make it possible to obtain an excellent photoelectric conversion characteristic. Furthermore, it was possible to verify that a particularly outstanding excellent performance was exhibited in photoelectric conversion under weak light such as room light. This photoelectric conversion is a scarcely reported case.

Specific exemplary compounds of general formula (3) above are presented below. However, these compounds are non-limiting examples. When the structural formulae presented below have a number beside, the number indicates a compound number in "Japan Chemical Substance Dictionary", which is a chemical substance database open to the public by Japan Science and Technology Agency.

Compound No. 2-1

J31.394G

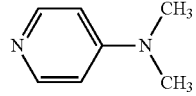

Compound No. 2-2

J2.748.250C

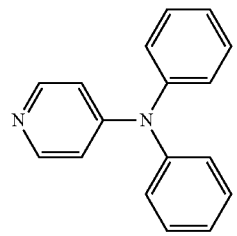

-continued

Compound No. 2-3

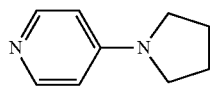

Compound No. 2-4

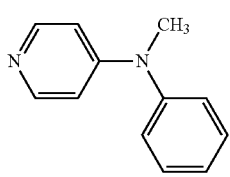

Compound No. 2-5

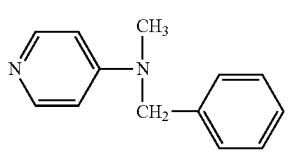

Compound No. 2-6

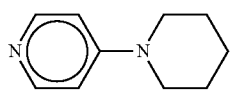

Compound No. 2-7

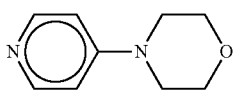

Compound No. 2-8

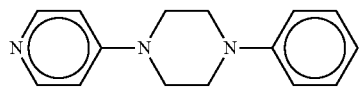

Compound No. 2-9

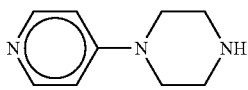

An amount of the basic compound represented by general formula (3) added in the hole transport layer is preferably 1 part by mass or greater but 20 parts by mass or less and more preferably 5 parts by mass or greater but 15 parts by mass or less relative to 100 parts by mass of the organic hole transport material.

With a view to improving conductivity, an oxidizing agent for changing part of the organic hole transport material to a radical cation may be added.

Examples of the oxidizing agent include tris(4-bromophenyl)aminium hexachloroantimonate, silver hexafluoroantimonate, nitrosonium tetrafluoroborate, silver nitrate, and cobalt complex-based compounds.

There is no need that the whole of the organic hole transport material be oxidized by addition of the oxidizing agent. Only part of the organic hole transport material needs to be oxidized. It is optional whether the added oxidizing agent is removed or not to the outside of the system after addition.

It is preferable that the hole transport layer 6 be formed directly on the electron transport layer 4. A method for producing the hole transport layer 6 is not particularly limited. Examples of the method include a method for forming a thin film in vacuum, such as vacuum vapor deposition, and a wet film forming method. Considering production costs and other factors, the wet film forming method is particularly preferable, and a method for coating the electron transport layer with the hole transport layer is preferable.

In using the wet film forming method, a coating method is not particularly limited and may be performed according to a known method. For example, it is possible to use a dipping method, a spraying method, a wire bar method, a spin coating method, a roller coating method, a blade coating method, a gravure coating method, and wet printing methods including various methods such as letterpress, offset, gravure, intaglio, rubber plate, and screen printing. Film formation may be performed under a supercritical fluid or a subcritical fluid having a temperature/pressure lower than a critical point.

The supercritical fluid is not particularly limited and may be appropriately selected depending on the intended purpose so long as the supercritical fluid exists as a non-condensable high-density fluid in temperature and pressure ranges higher than a limit (critical point) until which a gas and a liquid can coexist, and even when compressed, does not condense but is maintained at higher than or equal to a critical temperature and higher than or equal to a critical pressure. However, a supercritical fluid having a low critical temperature is preferable.

Preferable examples of the supercritical fluid include carbon monoxide, carbon dioxide, ammonia, nitrogen, water, alcohol-based solvents such as methanol, ethanol, and n-butanol, hydrocarbon-based solvents such as ethane, propane, 2,3-dimethylbutane, benzene, and toluene, halogen-based solvents such as methylene chloride and chlorotrifluoromethane, and ether-based solvents such as dimethyl ether. Among these supercritical fluids, carbon dioxide is particularly preferable because carbon dioxide has a critical pressure of 7.3 MPa and a critical temperature of 31° C., and hence can form a supercritical state easily and is incombustible and easy to handle.

One of these fluids may be used alone or two or more of these fluids may be used as a mixture.

The subcritical fluid is not particularly limited and may be appropriately selected depending on the intended purpose so long as the subcritical fluid exists as a high-pressure liquid in temperature and pressure ranges near critical points.

The compounds presented above as examples of the supercritical fluid can also be used favorably as the subcritical fluid.

A critical temperature and a critical pressure of the supercritical fluid are not particularly limited and may be appropriately selected depending on the intended purpose. However, the critical temperature is preferably −273 degrees C. or higher but 300 degrees C. or lower and particularly preferably 0 degrees C. or higher but 200 degrees C. or lower.

In addition to the supercritical fluid and the subcritical fluid, an organic solvent and an entrainer may further be used in combination.

Addition of an organic solvent and an entrainer makes it easier to adjust solubility to the supercritical fluid.

The organic solvent is not particularly limited and may be appropriately selected depending on the intended purpose. Examples of the organic solvent include:

ketone-based solvents such as acetone, methyl ethyl ketone, and methyl isobutyl ketone;

ester-based solvents such as ethyl formate, ethyl acetate, and n-butyl acetate;

ether-based solvents such as diisopropyl ether, dimethoxyethane, tetrahydrofuran, dioxolane, and dioxane;

amide-based solvents such as N,N-dimethylformamide, N,N-dimethylacetamide, and N-methyl-2-pyrrolidone;

halogenated hydrocarbon-based solvents dichloromethane, chloroform, bromoform, methyl iodide, dichloroethane, trichloroethane, trichloroethylene, chlorobenzene, o-dichlorobenzene, fluorobenzene, bromobenzene, iodobenzene, and 1-chloronaphthalene; and hydrocarbon-based solvents such as n-pentane, n-hexane, n-octane, 1,5-hexadiene, cyclohexane, methylcyclohexane, cyclohexadiene, benzene, toluene, o-xylene, m-xylene, p-xylene, ethylbenzene, and cumene.

In the present disclosure, a press process step may be provided after the hole transport layer 6 is provided on the first electrode. It is considered that the press process makes close adhesion of the organic hole transport material with the porous electrode stronger to improve efficiency.

A method for the press process is not particularly limited. Examples of the method include a press forming method using a flat plate represented by an IR tablet molding machine, and a roll press method using, for example, a roller.

A pressure is preferably 10 kgf/cm$^2$ or higher and more preferably 30 kgf/cm$^2$ or higher. A time for which the press process is performed is not particularly limited. However, the time is preferably within 1 hour. Heat may be applied during the press process.

In the press process, a release material may be interposed between a press machine and the electrode.

Examples of a material used as the release material include fluororesins such as polytetrafluoroethylene, polychlorotrifluoroethylene, tetrafluoroethylene-hexafluoropropylene copolymers, perfluoroalkoxy fluoride resins, polyvinylidene fluoride, ethylene-tetrafluoroethylene copolymers, ethylene-chlorotrifluoroethylene copolymers, and polyvinyl fluoride.

After the press process step, a metal oxide may be provided between the organic hole transport material and the second electrode, before the counter electrode is provided. Examples of the metal oxide that may be provided include molybdenum oxide, tungsten oxide, vanadium oxide, and nickel oxide. Among these metal oxides, the molybdenum oxide is particularly preferable.

A method for providing the metal oxide on the hole transport material is not particularly limited. Examples of the method include methods for forming a thin film in vacuum, such as sputtering and vacuum vapor deposition, and a wet film forming method.

As the wet film forming method, a method of preparing a paste in which powder or sol of the metal oxide is dispersed, and coating the hole transport layer with the paste is preferable.

In using the wet film forming method, a coating method is not particularly limited and may be performed according to a known method.

For example, it is possible to use a dipping method, a spraying method, a wire bar method, a spin coating method, a roller coating method, a blade coating method, a gravure coating method, and wet printing methods including various methods such as letterpress, offset, gravure, intaglio, rubber plate, and screen printing. A film thickness of the metal oxide is preferably from 0.1 nm through 50 nm and more preferably from 1 nm through 10 nm.

<Second Electrode>

The second electrode is newly imparted after the hole transport layer is formed or on the metal oxide described above.

Typically, the same configuration as the first electrode described above can be used as the second electrode. A support is not indispensable for a configuration of which strength and seal can be sufficiently maintained.

Specific examples of the material of the second electrode include: metals such as platinum, gold, silver, copper, and aluminum; carbon-based compounds such as graphite, fullerene, carbon nanotube, and graphene; conductive metal oxides such as ITO, FTO, and ATO; and conductive polymers such as polythiophene and polyaniline.

A film thickness of the second electrode layer is not particularly limited. One material may be used alone or two or more materials may be used as a mixture.

Formation of the second electrode by coating can be performed by appropriate methods such as coating, lamination, vapor deposition, CVD, and pasting on the hole transport layer, depending on the kind of the material used and the kind of the hole transport layer.

In order to realize an operation as a dye-sensitized solar cell, at least one of the first electrode and the second electrode needs to be substantially transparent.

In the photoelectric conversion element of the present disclosure, the first electrode is transparent. A preferable manner is that the sunlight is made incident from the first electrode side. In this case, it is preferable to use a light-reflecting material at the second electrode side. Metals, glass on which a conductive oxide is vapor-deposited, plastics, and metallic thin films are preferable.

Providing an antireflection layer at the sunlight incident side is an effective means.

<Applications>

The photoelectric conversion element of the present disclosure can be applied to a solar cell and a power supply device including a solar cell.

Application examples include all devices that hitherto have utilized a solar cell or a power supply device using a solar cell.

The photoelectric conversion element may be used as, for example, a solar cell for a desk-top electronic calculator or a wristwatch. However, a power supply device for, for example, a portable phone, an electronic organizer, and an electronic paper can be presented as an example that takes advantage of the characteristic of the photoelectric conversion element of the present disclosure. Furthermore, an auxiliary power supply intended for extending a continuously usable time of rechargeable or dry cell-operated electric appliances can be presented as an application example. Moreover, a primary battery alternative combined with a secondary battery can also be presented as an application example as a stand-alone power system for a sensor.

Synthesis Example of Compound Represented by General Formula (1) Used in the Present Disclosure The compound can be easily synthesized according to a route presented below, as in an organic synthesis report example (J. Org. Chem. Soc., 67 (2002) 3029).

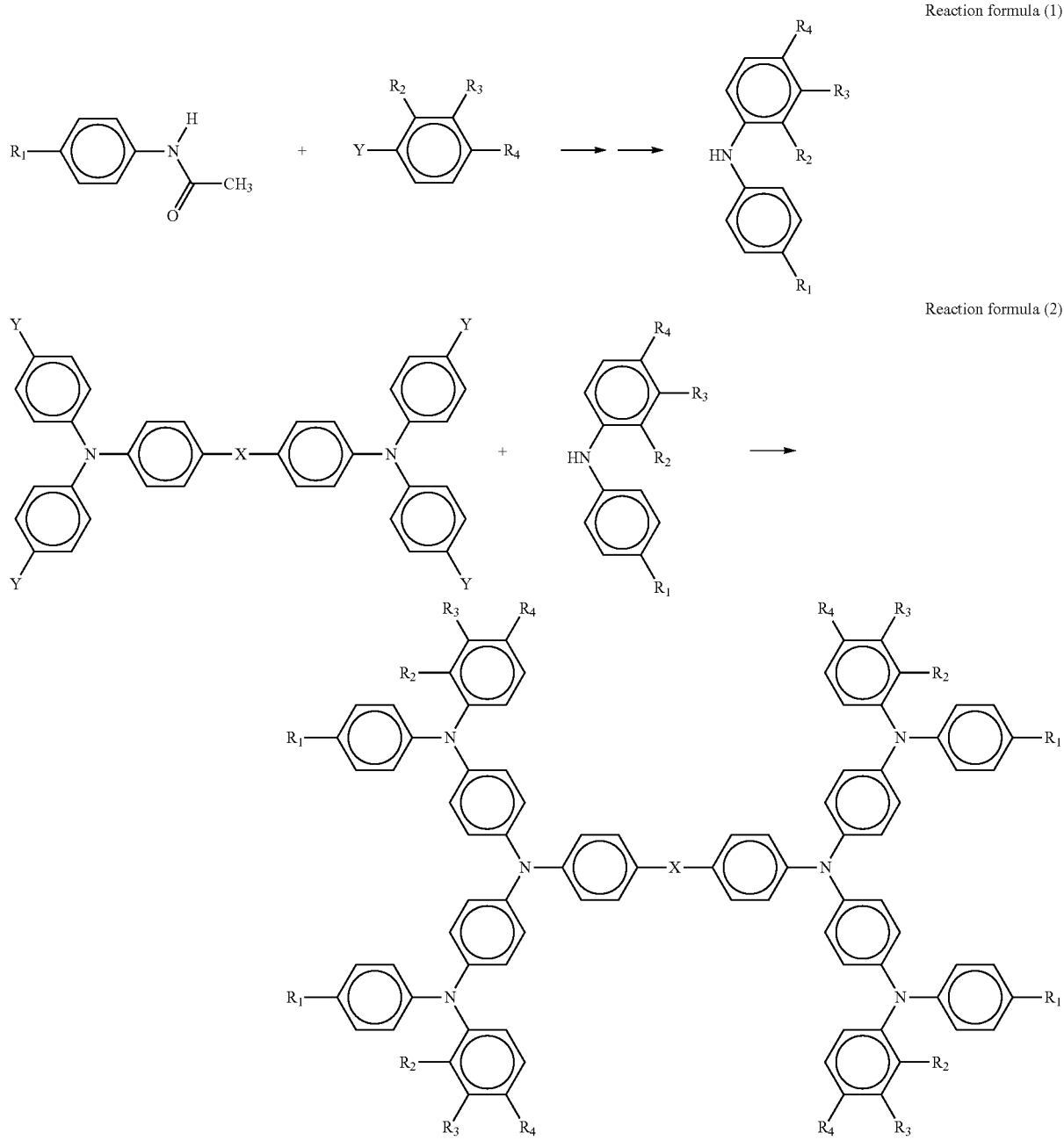

Reaction formula (1)

Reaction formula (2)

(In the formula, $R_1$ represents a methoxy group or an ethoxy group, $R_2$ represents a hydrogen group or a methyl group, $R_3$ represents a hydrogen group, a methyl group, or a methoxy group, $R_4$ represents a methoxy group, X represents —$CH_2$—, —$CH_2CH_2$—, —O—, or —$C(CH_2)_5$—, and Y represents a halogen element.)

Synthesis Example of Basic Material Used in the Present Disclosure

The basic material can be easily synthesized according to a route presented below, as in an organic synthesis report example (J. Org. Chem. Soc., 67 (2002) 3029).

Reaction formula (3)

(In the formula, $R_5$ and $R_6$ represent a substituted or unsubstituted alkyl group or aromatic hydrocarbon group, and may be the same as or different from each other. $R_5$ and $R_6$ may bind with each other to form a substituted or unsubstituted heterocyclic group containing a nitrogen atom. Z represents a halogen element.)

EXAMPLES

The present disclosure will be more specifically described below by way of Examples. However, the present disclosure should not be construed as being limited to the Examples.

Example 1

<Production of Titanium Oxide Semiconductor Electrode>

Reactive sputter by an oxygen gas using a target formed of metal titanium was performed to form a dense hole blocking layer 3 formed of titanium oxide on an ITO-based glass substrate.

Next, titanium oxide (P90 available from Nippon Aerosil Co., Ltd.) (3 g), acetylacetone (0.2 g), and a surfactant (polyoxyethylene octylphenyl ether available from Wako Pure Chemical Industries, Ltd.) (0.3 g) were subjected to a bead mill treatment for 12 hours together with water (5.5 g) and ethanol (1.0 g).

Polyethylene glycol (#20,000) (1.2 g) was added to the obtained dispersion liquid, to produce a paste.

This paste was coated on the hole blocking layer to have a film thickness of 1.5 micrometers, dried at room temperature, and then fired in the air at 500 degrees C. for 30 minutes, to form a porous electron transport layer 4.

<Production of Photoelectric Conversion Element>

The titanium oxide semiconductor electrode described above was immersed in the photosensitizing compound 5, which was D102 available from Mitsubishi Paper Mills Limited and represented by structural formula (5) above (0.5 mM, an acetonitrile/t-butanol (at a volume ratio of 1:1) solution), and left to stand still for 1 hour in a dark place, to adsorb the photosensitizing compound 5.

A solution obtained by adding the organic hole transport material presented as the exemplary compound No. 1-1 (183.1 mg), lithium bis(trifluoromethanesulfonyl)imide available from Kanto Chemical Co., Inc. (12.83 mg), and tertial butylpyridine (tBP) available from Sigma Aldrich Co., LLC. (21.97 mg) in a chlorobenzene solution (1 ml) was spin-coated on the titanium oxide semiconductor electrode supporting the photosensitizing compound 5, to form a hole transport layer 6 (with a film thickness of 300 nm). Silver was formed on the hole transport layer to have a thickness of 100 nm by vacuum vapor deposition to form a second electrode 7. In this way, a photoelectric conversion element was produced.

<Evaluation of Photoelectric Conversion Element>

The photoelectric conversion efficiency of the obtained photoelectric conversion element under white LED irradiation (50 Lux: 12.5 microwatts/cm$^2$ and 10 Lux: 2.5 microwatts/cm$^2$) was measured. The measurement was performed using a desk lamp CDS-90a (study mode) available from Cosmotechno. Co., Ltd. as the white LED, and a solar cell evaluation system AS-510-PV03 available from NF Corporation as an evaluator. The results are presented in Tables 1-2 and 1-3.

Examples 2 to 14

Photoelectric conversion elements were produced in the same manner as in Example 1, except that the compound No. 1-1 and tertial butylpyridine (tBP) used in Example 1 were changed as presented in Table 1-1. The photoelectric conversion elements were evaluated, and the results are presented in Tables 1-2 and 1-3.

Comparative Example 1

A photoelectric conversion element was produced in the same manner as in Example 1, except that the compound No. 1-1 used in Example 1 was changed to an organic hole transport material (available from Merck Japan, brand name: 2,2',7,7'-tetrakis(N,N-di-p-methoxyphenylamino)-9,9'-spirobifluorene, product number: SHT-263). The photoelectric conversion element was evaluated, and the results are presented in Tables 1-2 and 1-3.

Comparative Example 2

A photoelectric conversion element was produced in the same manner as in Example 3, except that the compound No. 1-1 used in Example 3 was changed to an organic hole transport material (available from Merck Japan, brand name: 2,2',7,7'-tetrakis(N,N-di-p-methoxyphenylamino)-9,9'-spirobifluorene, product name: SHT-263). The photoelectric conversion element was evaluated, and the results are presented in Tables 1-2 and 1-3.

TABLE 1-1

| | Compound No. | |
| --- | --- | --- |
| | Organic hole transport agent | Basic material |
| Ex. 1 | 1-1 | tBP |
| Ex. 2 | 1-1 | 2-1 |
| Ex. 3 | 1-1 | 2-3 |
| Ex. 4 | 1-1 | 2-5 |
| Ex. 5 | 1-1 | 2-6 |
| Ex. 6 | 1-1 | 2-7 |
| Ex. 7 | 1-2 | 2-3 |
| Ex. 8 | 1-2 | 2-7 |
| Ex. 9 | 1-3 | 2-3 |
| Ex. 10 | 1-3 | 2-6 |
| Ex. 11 | 1-4 | 2-3 |
| Ex. 12 | 1-5 | 2-3 |
| Ex. 13 | 1-6 | 2-3 |
| Ex. 14 | 1-7 | 2-3 |
| Comp. Ex. 1 | SHT263 | tBP |
| Comp. Ex. 2 | SHT263 | 2-3 |

TABLE 1-2

| | 50 Lux (12.5 microwatts/cm$^2$) | | | |
| --- | --- | --- | --- | --- |
| | Open circuit voltage (V) | Short-circuiting current density (microampere/cm$^2$) | Fill factor | Conversion efficiency (%) |
| Ex. 1 | 0.708 | 2.98 | 0.71 | 11.98 |
| Ex. 2 | 0.857 | 3.35 | 0.75 | 17.23 |
| Ex. 3 | 0.868 | 3.37 | 0.75 | 17.55 |
| Ex. 4 | 0.855 | 3.29 | 0.75 | 16.88 |
| Ex. 5 | 0.863 | 3.31 | 0.76 | 17.37 |
| Ex. 6 | 0.871 | 3.38 | 0.75 | 17.66 |
| Ex. 7 | 0.872 | 3.39 | 0.76 | 17.97 |
| Ex. 8 | 0.873 | 3.32 | 0.75 | 17.39 |
| Ex. 9 | 0.859 | 3.43 | 0.76 | 17.91 |
| Ex. 10 | 0.858 | 3.39 | 0.75 | 17.45 |
| Ex. 11 | 0.871 | 3.27 | 0.76 | 17.32 |
| Ex. 12 | 0.870 | 3.32 | 0.76 | 17.56 |
| Ex. 13 | 0.874 | 3.35 | 0.76 | 17.80 |
| Ex. 14 | 0.871 | 3.38 | 0.76 | 17.90 |
| Comp. Ex. 1 | 0.712 | 2.87 | 0.69 | 11.28 |
| Comp. Ex. 2 | 0.871 | 3.48 | 0.74 | 17.94 |

TABLE 1-3

| | 10 Lux (2.5 microwatts/cm$^2$) | | | |
|---|---|---|---|---|
| | Open circuit voltage (V) | Short-circuiting current density (microampere/cm$^2$) | Fill factor | Conversion efficiency (%) |
| Ex. 1 | 0.653 | 0.572 | 0.73 | 10.91 |
| Ex. 2 | 0.808 | 0.701 | 0.77 | 17.45 |
| Ex. 3 | 0.812 | 0.708 | 0.77 | 17.71 |
| Ex. 4 | 0.810 | 0.698 | 0.78 | 17.64 |
| Ex. 5 | 0.811 | 0.704 | 0.77 | 17.59 |
| Ex. 6 | 0.812 | 0.709 | 0.77 | 17.73 |
| Ex. 7 | 0.815 | 0.710 | 0.77 | 17.82 |
| Ex. 8 | 0.813 | 0.709 | 0.78 | 17.98 |
| Ex. 9 | 0.810 | 0.715 | 0.78 | 18.07 |
| Ex. 10 | 0.809 | 0.711 | 0.78 | 17.95 |
| Ex. 11 | 0.812 | 0.792 | 0.77 | 19.81 |
| Ex. 12 | 0.816 | 0.781 | 0.78 | 19.88 |
| Ex. 13 | 0.815 | 0.772 | 0.78 | 19.63 |
| Ex. 14 | 0.812 | 0.759 | 0.78 | 19.23 |
| Comp. Ex. 1 | 0.628 | 0.553 | 0.62 | 8.61 |
| Comp. Ex. 2 | 0.793 | 0.697 | 0.69 | 15.26 |

Example 15

A photoelectric conversion element was produced in the same manner as in Example 1, except that lithium bis(trifluoromethanesulfonyl)imide used in Example 1 was changed to 1-n-hexyl-3-methylimidazoliniumbis(trifluoromethylsulfonyl)imide. The photoelectric conversion element was evaluated The results at 50 Lux were indicated as excellent characteristics including an open circuit voltage of 0.701 V, a short-circuiting current density of 3.02 microamperes/cm$^2$, a fill factor of 0.72, and a conversion efficiency of 12.12%. The results at 10 Lux were indicated as an open circuit voltage of 0.648 V, a short-circuiting current density of 0.591 microamperes/cm$^2$, a fill factor of 0.64, and a conversion efficiency of 9.80%.

The photoelectric conversion elements of Examples 1 to 15 were found to have an excellent power generation performance in an environment with an ultra-weak illuminance (from 10 Lux through 50 Lux). Particularly, these photoelectric conversion elements were better in power generation performance in the 10 Lux environment, compared with the organic hole transport material (SHT-263) used in Comparative Examples 1 and 2. It is undesirable to employ Comparative Example 2, because Comparative Example 2 had a larger performance difference between 50 Lux and 10 Lux, compared with Example 3. Furthermore, the compound represented by general formula (1) had a greater advantage over SHT263, considering the material cost of SHT263.

In indoor places such as corridors where the illuminance is low, the walls are often at about 10 Lux. Hence, these photoelectric conversion elements are considered useful as stand-alone power systems for sensors in the field of security such as human sensors.

As clear from the above, it can be understood that the photoelectric conversion element of the present disclosure exhibits an excellent photoelectric conversion characteristic under an ultra-weak illuminance.

Aspects of the present invention are as follows, for example.

<1> A photoelectric conversion element including:
a first electrode;
a hole blocking layer;
an electron transport layer;
a hole transport layer; and
a second electrode,
wherein the hole transport layer contains a compound represented by general formula (1) below, General formula (1)

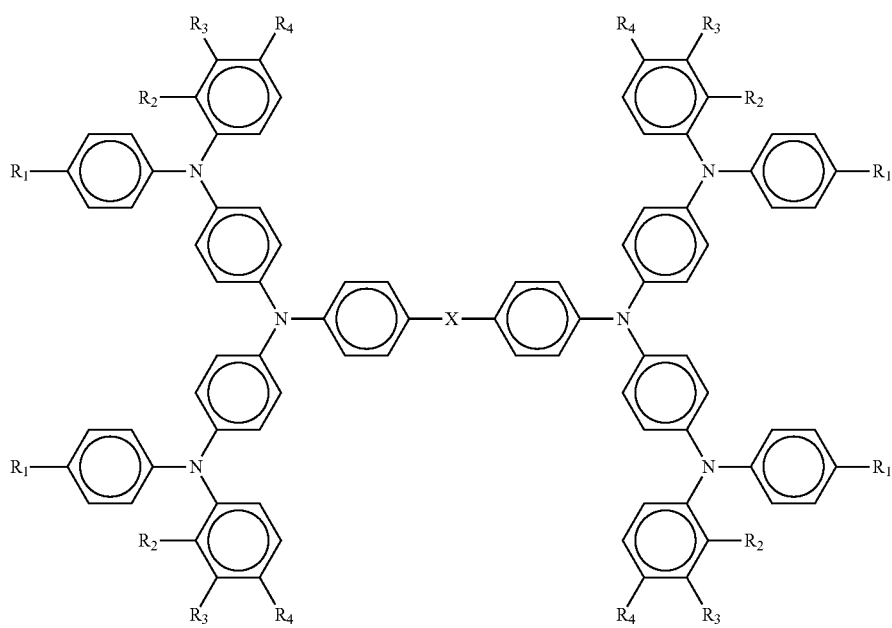

where in the formula, $R_1$ represents a methoxy group or an ethoxy group, $R_2$ represents a hydrogen group or a methyl group, $R_3$ represents a hydrogen group, a methyl group, or a methoxy group, $R_4$ represents a methoxy group, and X represents —$CH_2$—, —$CH_2CH_2$—, —O—, or —C($CH_2$)$_5$—.

<2> The photoelectric conversion element according to <1>, wherein the hole transport layer contains a basic compound represented by general formula (2) below, General formula (2)

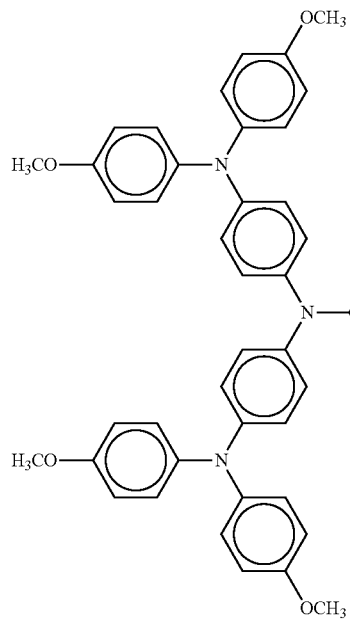
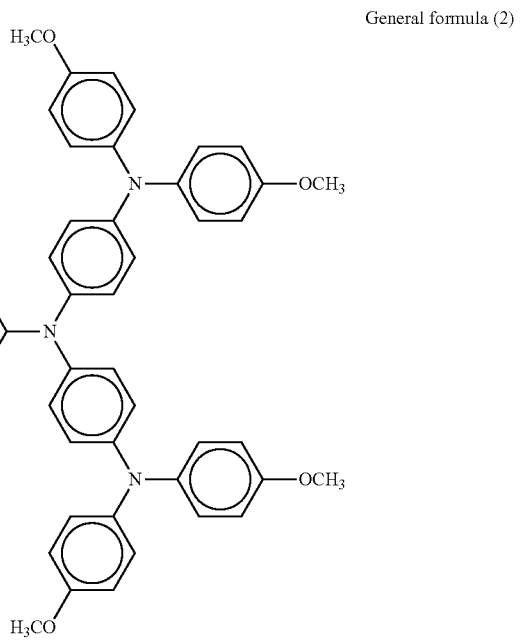

where in the formula, X represents —CH$_2$—, —CH$_2$CH$_2$—, —O—, or —C(CH$_2$)$_5$—.

<3> The photoelectric conversion element according to <1> or <2>, wherein the hole transport layer contains a basic compound represented by general formula (3) below, General formula (3)

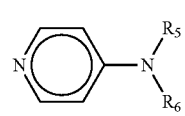

where in the formula, R$_5$ and R$_6$ represent a substituted or unsubstituted alkyl group or aromatic hydrocarbon group, and may be the same as or different from each other, and R$_5$ and R$_6$ may bind with each other to form a substituted or unsubstituted heterocyclic group containing a nitrogen atom.

<4> The photoelectric conversion element according to any one of <1> to <3>,
wherein the electron transport layer contains an electron transport material, and
wherein the electron transport material is at least one selected from the group consisting of titanium oxide, zinc oxide, tin oxide, and niobium oxide.

<5> The photoelectric conversion element according to any one of <1> to <4>,
wherein the hole blocking layer contains titanium oxide.

<6> The photoelectric conversion element according to any one of <1> to <5>,
wherein the hole transport layer further contains an imidazolium compound, which is an ionic liquid.

<7> The photoelectric conversion element according to any one of <1> to <6>,
wherein the photoelectric conversion element is used as a solar cell.

What is claimed is:

1. A photoelectric conversion element, comprising:
a first electrode;
an electron transport layer;
a hole transport layer; and
a second electrode,
wherein the hole transport layer comprises a compound represented by general formula (1) below, general formula (1)

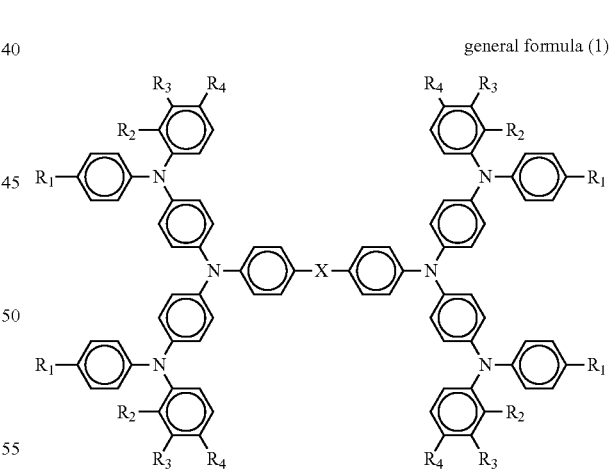

wherein, in general formula (1), R$_1$ represents a methoxy group or an ethoxy group, R$_2$ represents a hydrogen group or a methyl group, R$_3$ represents a hydrogen group, a methyl group, or a methoxy group, R$_4$ represents a methoxy group, and X represents —CH$_2$—, —CH$_2$C—, or —C(CH$_2$)$_5$—.

2. The photoelectric conversion element according to claim 1, wherein the compound represented by general formula (1) is represented by general formula (2) below,

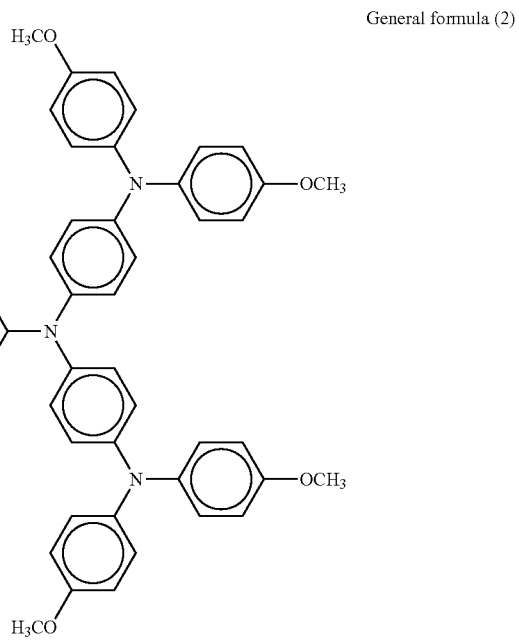

General formula (2)

wherein, in general formula (2), X represents —CH$_2$—, —CH$_2$—, —CH$_2$CH$_2$—, —O—, or —C(CH$_2$)$_5$—.

3. The photoelectric conversion element according to claim 1, wherein the hole transport layer further comprises a basic compound represented by general formula (3) below,

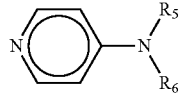

general formula (3)

wherein, in general formula (3), R$_5$ and R$_6$ represent a substituted or unsubstituted alkyl group or aromatic hydrocarbon group, and may be same as or different from each other, and R$_5$ and R$_6$ may bind with each other to form a substituted or unsubstituted heterocyclic group that comprises a nitrogen atom.

4. The photoelectric conversion element according to claim 1, wherein the electron transport layer comprises an electron transport material, and wherein the electron transport material comprises at least one selected from the group consisting of titanium oxide, zinc oxide, tin oxide, and niobium oxide.

5. The photoelectric conversion element according to claim 1, wherein the hole transport layer further comprises an imidazolium compound, which is an ionic liquid.

6. A solar cell, comprising the photoelectric conversion element according to claim 1.

7. The photoelectric conversion element according to claim 1, wherein, in general formula (1), R$_1$ represents a methoxy group.

8. The photoelectric conversion element according to claim 1, wherein, in general formula (1), R$_1$ represents an ethoxy group.

9. The photoelectric conversion element according to claim 1, wherein, in general formula (1), R$_2$ represents a hydrogen group.

10. The photoelectric conversion element according to claim 1, wherein, in general formula (1), R$_2$ represents a methyl group.

11. The photoelectric conversion element according to claim 1, further comprising:

a hole blocking layer between the first electrode and the electron transport layer.

12. The photoelectric conversion element according to claim 11, wherein the hole blocking layer comprises titanium oxide.

13. The photoelectric conversion element according to claim 11, wherein the content of the compound represented by general formula (1) in the hole transport layer is in a range of from 40% by mass through 90% by mass.

14. The photoelectric conversion element according to claim 1, wherein the hole transport layer further comprises a lithium compound.

15. The photoelectric conversion element according to claim 1, wherein, in general formula (1), X represents —CH$_2$—.

16. The photoelectric conversion element according to claim 1, wherein, in general formula (1), X represents —CH$_2$CH$_2$—.

17. The photoelectric conversion element according to claim 1, wherein the compound represented as by general formula (1) is represented

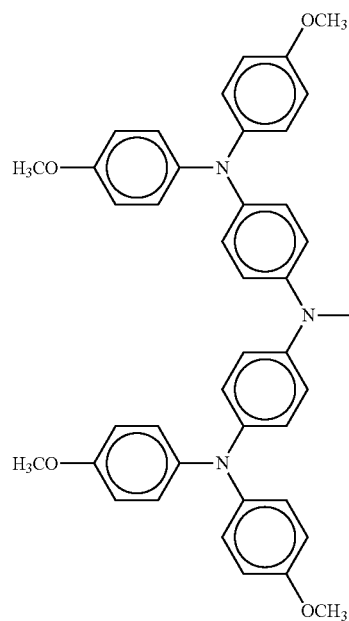
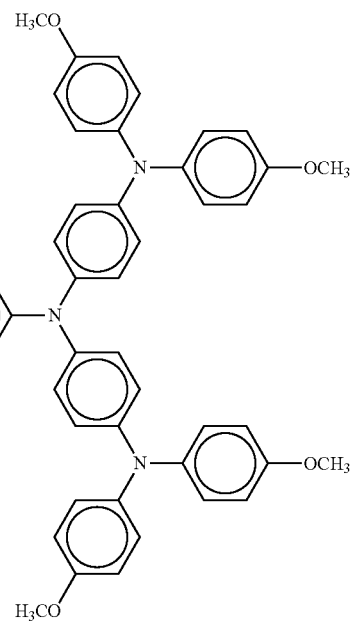
wherein X is —CH$_2$—.
18. The photoelectric conversion element according to claim 1, wherein the compound represented as by general formula (1) is represented
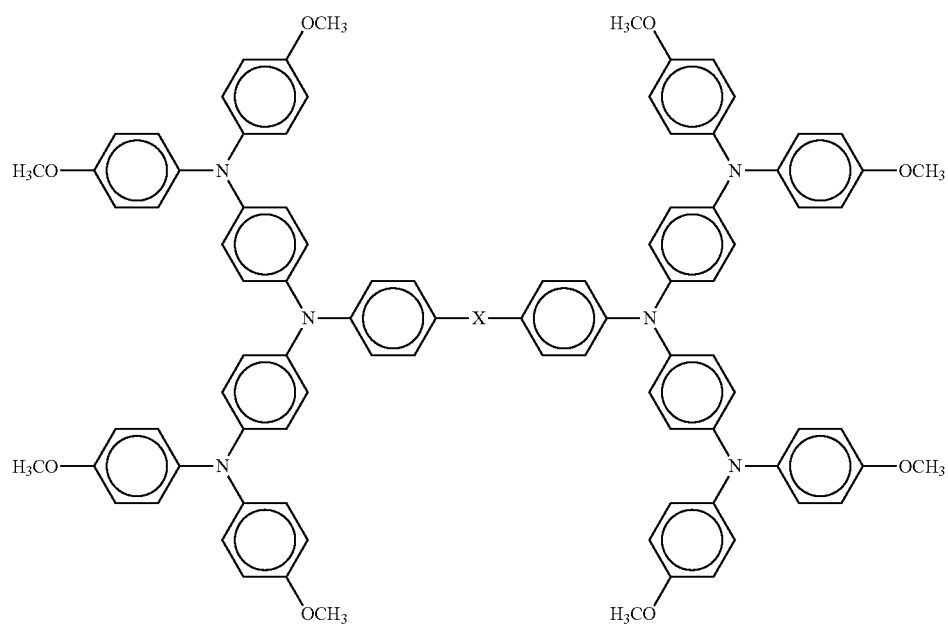
wherein X is —CH$_2$CH$_2$—.

19. The photoelectric conversion element according to claim 1, wherein the compound represented as by general formula (1) is represented
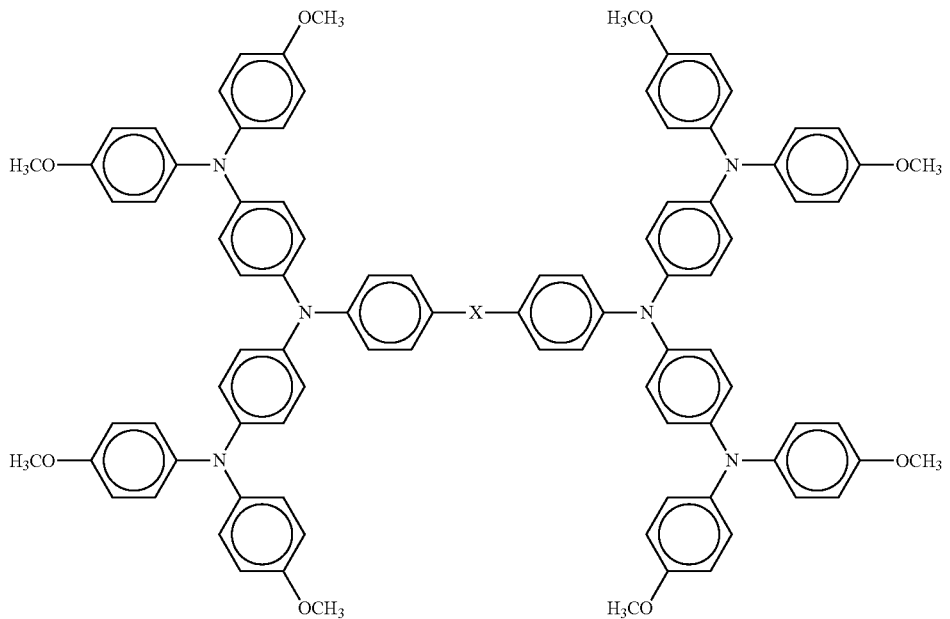
wherein X is —O—.
20. The photoelectric conversion element according to claim 1, wherein the compound represented as by general formula (I) is represented
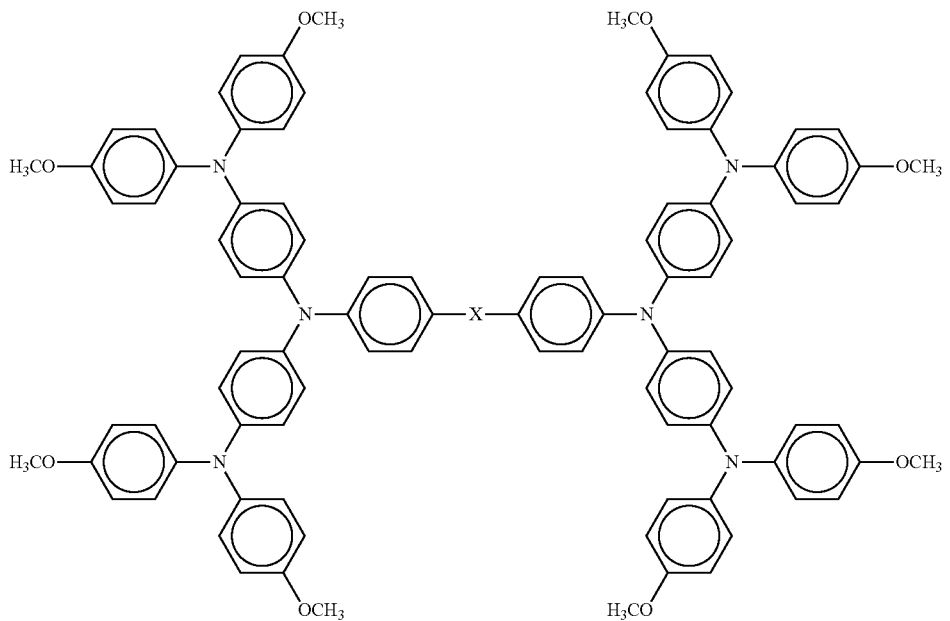
wherein X is —C(CH$_2$)$_5$—.
* * * * *